United States Patent
Wei

(10) Patent No.: US 10,441,948 B2
(45) Date of Patent: Oct. 15, 2019

(54) RUTHENIUM- OR OSMIUM-BASED COMPLEX CATALYSTS

(71) Applicant: ARLANXEO DEUTSCHLAND GMBH, Dormagen (DE)

(72) Inventor: Zhenli Wei, Masai Johor (MY)

(73) Assignee: ARLANXEO DEUTSCHLAND GMBH, Dormagen (DE)

( * ) Notice: Subject to any disclaimer, the term of this patent is extended or adjusted under 35 U.S.C. 154(b) by 0 days.

(21) Appl. No.: 15/566,373

(22) PCT Filed: Apr. 12, 2016

(86) PCT No.: PCT/EP2016/058009
§ 371 (c)(1),
(2) Date: Oct. 13, 2017

(87) PCT Pub. No.: WO2016/166097
PCT Pub. Date: Oct. 20, 2016

(65) Prior Publication Data
US 2018/0290134 A1 Oct. 11, 2018

(30) Foreign Application Priority Data
Apr. 16, 2015 (EP) .................................... 15163781

(51) Int. Cl.
*B01J 31/24* (2006.01)
*C07F 15/00* (2006.01)
*C08C 19/02* (2006.01)
*C08L 9/02* (2006.01)
*B01J 31/20* (2006.01)
*B01J 31/22* (2006.01)
*B01J 37/04* (2006.01)

(52) U.S. Cl.
CPC ........... *B01J 31/2404* (2013.01); *B01J 31/20* (2013.01); *B01J 31/2291* (2013.01); *B01J 31/2295* (2013.01); *B01J 37/04* (2013.01); *C07F 15/0046* (2013.01); *C08C 19/02* (2013.01); *C08L 9/02* (2013.01); *B01J 2231/645* (2013.01); *B01J 2531/821* (2013.01)

(58) Field of Classification Search
None
See application file for complete search history.

(56) References Cited

U.S. PATENT DOCUMENTS

| | | | |
|---|---|---|---|
| 2014/0228563 A1* | 8/2014 | Cazin | C07C 6/02 540/609 |
| 2015/0119530 A1 | 4/2015 | Liu et al. | |
| 2015/0166686 A1 | 6/2015 | Liu et al. | |

FOREIGN PATENT DOCUMENTS

| TW | 201334870 A1 | 9/2013 |
|---|---|---|
| TW | 201404465 A | 2/2014 |

* cited by examiner

*Primary Examiner* — Yun Qian
(74) *Attorney, Agent, or Firm* — Norris McLaughlin PA

(57) ABSTRACT

The present invention relates to ruthenium- or osmium-based complex structures, to the synthesis thereof and their use as catalysts for hydrogenating unsaturated substrates.

18 Claims, No Drawings

RUTHENIUM- OR OSMIUM-BASED COMPLEX CATALYSTS

FIELD OF THE INVENTION

The present invention relates to ruthenium- or osmium-based complex structures, to the synthesis thereof and their use as catalysts for hydrogenating unsaturated substrates.

BACKGROUND OF THE INVENTION

Ruthenium- or osmium-based catalysts play an important role in homogeneous hydrogenation reactions of various substrates for many years as summarized in the Handbook of Homogeneous Hydrogenation, 2007, Volume 1, Pages 45-70 (Edited by De Vries, Johannes G.; Elsevier, Cornelis J).

In recent years, novel types of five-coordinated ruthenium- or osmium-based catalysts have been developed.

In U.S. Pat. No. 5,057,581, a ruthenium-based complex of the formula (A) is disclosed (column 3, line 52). These complexes are used as selective hydrogenation catalysts for carbon-carbon double bonds.

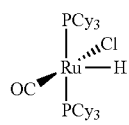

(A)

In WO 2013/159366 A1, catalysts with a general formula (B) as shown below are disclosed. The ligand $L^1$ represents a NHC-ligand such as N,N'-bis[2,4,6-(trimethyl)phenyl]imidazolidin-2-ylidene (SIMes) and $L^2$ represents either the same ligand as $L^1$, another NHC-ligand or a phosphine ligand such as $PCy_3$ (formula (B.a)). These catalysts are used for preparing hydrogenated nitrile rubbers.

However, this catalyst has disadvantages, as it is limited in stability in humidified air.

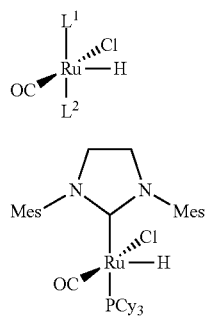

(B)

(B.a)

In H. M. Lee, D. C. Smith, Jr, Z. He, E. D. Stevens, C. S. Yi, S. P. Nolan. Organometallics, 2001, 20 (4), 794-797 and N. J. Beach, J. M. Blacquiere, S. D. Drouin and D. E. Fogg. Organometallics, 2009, 28 (2), 441-447, mixed NHC-phosphine variants of the type $RuHCl(CO)(PR_3)(NHC)$ are disclosed, e.g. $RuHCl(CO)(PCy_3)(IMes)$ (formula (B.b)). It was found that the use of labile phosphines in combination with strongly donating NHCs had a positive effect on rates of catalysis.

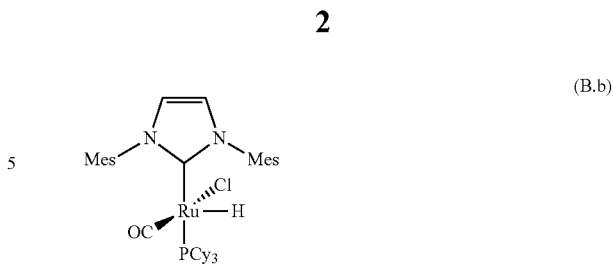

(B.b)

In Mücke, P., Linseis, M., Zális, S., Winter, R. F. Inorganica Chmca Acta 374 (2011) 36-50, a ruthenium-based complex of the formula (C) is disclosed. The meaning for the R moiety is not limited unless it is not too bulky (page 41). No NHC ligands are disclosed as alternative substituents. The document is silent about the use of this complex for hydrogenation reactions. The use of the complex as a catalyst in the presence of a nitrile rubber polymer is not disclosed.

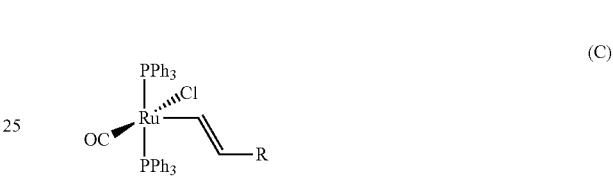

(C)

In Wilton-Ely, J. D. E. T, Pogorzeloc, P. J., Honarkhah, S. J., Reid, D. H., Tocher, D. A. Organometallics, 2005, 24, 2862-2874, a ruthenium-based complex of the formula (D) is disclosed (page 2869, Scheme 4). The meaning of the R moiety can be H or C=CHPh and the meaning of the R' moiety can be H, Ph or $CMe_3$. However, no complex comprising an NHC-ligand instead of the second phosphine ligand is disclosed. The document is silent about the use of the complex as a catalyst in hydrogenation reactions.

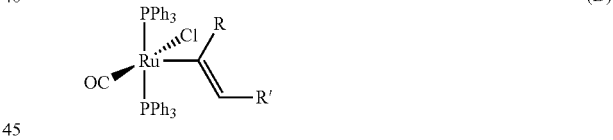

(D)

In Maurer, J., Linseis, M., Sarkar, B., Schwederski, B., Niemayer, M., Kaim, W., Zalis, S., Anson, C., Zable, M., Winter, R. F. J. Am. Chem. Soc. 2008, 130, 259-268, a ruthenium-based complex of the formula (E) comprising arylphosphine ligands is disclosed (page 260, structure 2a). However, no complex comprising an NHC-ligand instead of the second phosphine ligand is disclosed. The document does not mention the use of the complex as a catalyst in hydrogenation reactions.

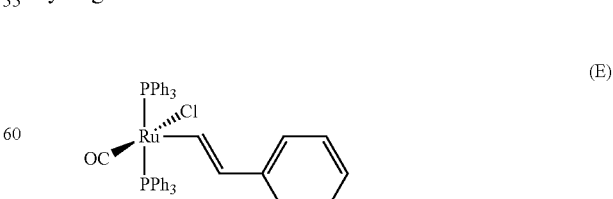

(E)

In Farmer, J. D., Man, W. Y., Fox, M. A., Yufit, D. S., Howard, J. A. K., Hill, A. F., Low, P. J. Journal of Organometallic Chemistry 721-722 (2012) 173-185, a ruthenium-based complex of the formula (F) comprising arylphosphine ligands is disclosed (page 175, Scheme 2). The meaning of the R moiety is limited to $N(C_5H_4Me-4)_2$, OMe, Me, $CO_2Me$ and $NO_2$. However, no structure is disclosed with a $PCy_3$ or a NHC-ligand. The use of the complexes as catalysts for hydrogenation reactions of unsaturated olefins is not disclosed.

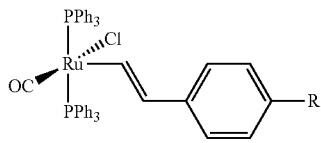

(F)

In Buil, M. L., Esteruelas, M. A., Goni, E., Olivan, M., Onate, E. Organometallics, 2006, 25, 3076-3083, a ruthenium-based complex of the formula (G) comprising alkylphosphine ligands is disclosed (page 3078, Complex 7). However, no structure is disclosed comprising a NHC-ligand and a (cyclohexyl)phosphine. Furthermore, the use of the complexes as catalysts for the hydrogenation reaction of olefins is not disclosed.

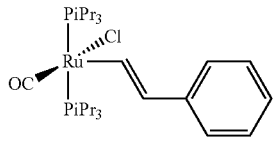

(G)

The formula (G) is disclosed also in Werner, H., Estrueias, M. A., Otto, H. Organometallics 1986, 5, 2295-2299.

In Marchenko, A. V., Gerard, H., Elsenstein, O., Caulton, K. G. New J. Chem., 2001, 25, 1244-1255, a ruthenium-based complex of the formula (H) comprising alkylphosphine ligands is disclosed (page 1244, complex 2). No structure is disclosed comprising a NHC-ligand instead of one phosphine ligand. The document is silent about the use of this complex as a catalyst for hydrogenation reactions of unsaturated olefins. However, the document mentions that five-coordinate, 16-electron square-pyramidal complexes $MHCl(CO)L_2$ ($L=Pr_3$) provide a rich variety of reactions with unsaturated hydrocarbons.

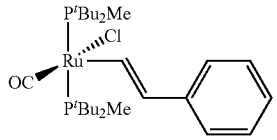

(H)

In Jung, S., Brandt, C. D., Wolf, J., Werner, H. Dalton Trans. 2004, 375-383, a ruthenium-based complex of the formula (J) is disclosed (page 376, structure 7). However, no NHC ligand is disclosed. The complexes described in this document are inactive as catalysts in olefin metathesis. The document is silent about the use of these complexes as hydrogenation catalysts.

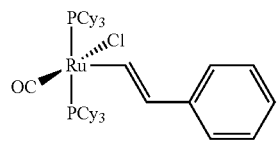

(J)

In Pan, Q., Rempel, G. L. Macromol. Rapid Commun. 2004, 25, 843-847, and in U.S. Pat. No. 5,057,581, a ruthenium-based complex of the above mentioned formula (J) is disclosed. The complex is used as a catalyst for the hydrogenation of Styrene-Butadiene Rubber. The hydrogenation is performed at temperatures of 135° C. and above. However, structures of the complex comprising a NHC-ligand instead of the second phosphine ligand are not disclosed. Furthermore, the use as a catalyst for nitrile rubber is not disclosed.

In Martin, P., McMagnus, N. T., Rempel, G. L. Journal of Molecular Catalysis A: Chemical 126 (1997) 115-131, ruthenium-based complexes of the above mentioned formulae (J) and (G) (page 116) are disclosed. These complexes have the hydrogenation activity at the same level as the $RuHCl(PCy_3)_2$ catalyst for the hydrogenation of C=C in nitrile-butadiene rubber. However, structures of the complex comprising a NHC-ligand instead of the second phosphine ligand are not disclosed.

In Chatwin, S. L., Mahon, M. F., Prior, T. J., Whittlesey, M. K. Inorganica Chimica Acta 363 (2010) 625-632, a ruthenium-based complex of the formula (K) (page 626, structure 8; as well as the description in section 2.4 on page 629) comprising NHC-ligands (IMes) as shown below is disclosed. The R moiety has the meaning of 2,4,6-trimethylphenyl. However, no use as a hydrogenation catalyst is disclosed as well as no complex structure comprising a(n) (alkyl)phosphine ligand.

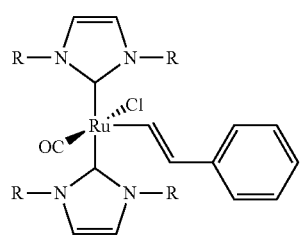

(K)

In Roper, W. R., Wright, L. J. Journal of organometallic chemistry 142(1) (1977) C1-C6, a ruthenium-based complex of the formula (L) comprising arylphosphine ligands is disclosed (page C2). No structure is disclosed comprising a NHC-ligand. The use of the complexes as catalysts for the hydrogenation of unsaturated olefins is not disclosed.

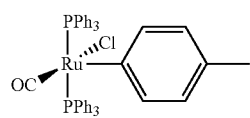

(L)

In Rickard, C. E. F., Roper, W. R., Taylor, G. E., Waters, J., Wright, L. J. Journal of Organometallic Chemistry, 389 (1990) 375-388, a ruthenium-based complex of the formula (M) comprising arylphosphine ligands is disclosed (page 377). No structure is disclosed comprising a NHC-ligand. The use of the complexes as catalysts for the hydrogenation of unsaturated olefins is not disclosed.

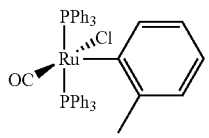

(M)

In Dinger, M. B., Mol, J. C. Organometallics 2003, 22, 1089-1095, a ruthenium-based complex of the formula (N) is disclosed (page 1090, structure 4). The complex was found to be an active and selective alkene double-bond isomerization catalyst. No structure is disclosed comprising an NHC-ligand. Furthermore, the document is silent about the use of the complex as a catalyst for the hydrogenation of unsaturated olefins, especially for the selective hydrogenation of nitrile rubbers.

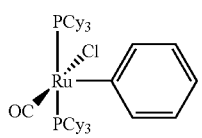

(N)

In Banti, D., Mol, J. C Journal of Organometallic Chemistry 689 (2004) 3113-3116, a ruthenium-based complex of the formula (O) comprising a NHC-ligand and a phosphine ligand is disclosed (page 3114, scheme 2, complex 5). In the NHC-ligand (SIPr), Dipp stands in all cases for 2,6-diisopropylphenyl. However, the document does not mention the activity of the complex as a catalyst for the hydrogenation of unsaturated olefins, especially nitrile rubbers.

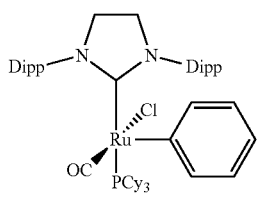

(O)

In Dinger, M. B., Mol, J. C. Eur. J. Inorg. Chem. 2003, 2827-2833, a ruthenium-based complex of the formula (P) is disclosed (page 2827, complex 7). The hydrogenation of a small terminal-olefin (1-octene) was tested at 100° C., 1 to 4 bar $H_2$ and a reaction time of 2 to 18 hours. The fully air-stable solid complex is described as an efficient hydrogenation catalyst at higher temperatures. Beside the hydrogenation product, the complex produces isomers. The hydrogenation activity of the complex towards the non-terminal olefin 2-octene is even lower. No complex structure is disclosed with a vinyl ligand which does not comprise a phenyl ring. The document is silent about the activity of the complex as a catalyst for the hydrogenation of nitrile rubbers.

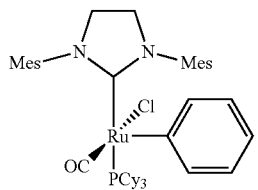

(P)

With regard to the hydrogenation of nitrile rubbers, the current industrial processes often use expensive Rh-based catalyst systems like Wilkinson's catalyst ($RhCl(PPh_3)_3$) together with $PPh_3$ as co-catalyst. After hydrogenation, extra time and costs must be spent to remove and recycle the expensive Rh-based catalyst.

It was therefore the object of the present invention to provide novel ruthenium- or osmium-based complexes which are excellent hydrogenation catalysts on the one hand and which show a high stability in air or water on the other hand. In particular, such complexes should provide a high hydrogenation activity for large-scale industrial use at ambient air reaction conditions.

An alternative object of the present invention was to provide a complex catalyst with such a high activity that no co-catalyst needs to be used anymore or recovery and recycling of the catalyst would no longer be necessary, resulting in catalyst costs reduction and subsequently in substantial process costs reduction. Compared to commercially available hydrogenated polymers as obtained nowadays with known catalysts, it is important that the hydrogenated polymers to be obtained by using any new complex catalyst must not show significant changes in the polymer properties and in its vulcanization behavior.

A further alternative object of the present invention was to overcome some of the problems of the state of the art catalysts, being: no gel formation, higher activity, higher stability in air or organic solution, higher stability over longer time, higher stability at elevated temperature, high hydrogenation activity at lower temperature and balancing between stability and activity.

This object has now been surprisingly solved by providing novel ruthenium- or osmium-based complexes comprising a phosphine ligand, a N-heterocyclic carbene ("NHC") ligand and a vinyl ligand.

SUMMARY OF THE INVENTION

The invention relates to novel complexes having the general formula (I)

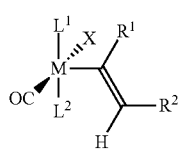

(I)

wherein
M represents ruthenium or osmium
X represents F, Cl, Br, I, —OH, —$CF_3$, pyridine, —$OC_6H_5$, —$CF_3COO^-$, —$CH_3SO_3$, or —$BF_4$,
$L^1$ represents a N-heterocyclic carbene (NHC) ligand,
$L^2$ represents a phosphine ligand,
$R^1$ represents hydrogen $R^2$ represents
- straight chain or branched, substituted or unsubstituted $C_1$-$C_{14}$-alkyl, preferably $C_1$-$C_8$-alkyl, more preferably methyl, ethyl, n-propyl, iso-propyl, n-butyl, iso-butyl, or tert.-butyl; or
- substituted or unsubstituted $C_3$-$C_{10}$-cycloalkyl, preferably $C_5$-$C_8$-cycloalkyl, more preferably cyclopentyl, cyclohexyl or cycloheptyl; or
- substituted or unsubstituted $C_6$-$C_{14}$-aryl, preferably $C_8$-$C_{10}$-aryl, more preferably phenyl, which is either unsubstituted or comprises 1, 2, 3, 4 or 5 identical or different substituents.

The novel complexes of general formula (I) can be prepared according to a novel process.

Hence the present invention also relates to processes for preparing the complexes of general formula (I).

The novel complexes of general formula (I) are excellently suited for hydrogenation reactions of unsaturated compounds.

Hence, the present invention comprises also the use of the complexes as catalysts for the hydrogenation of a broad variety of unsaturated compounds comprising at least one C═C double bond. Preferably, the complexes are used for the hydrogenation of nitrile rubbers. More preferably, the complexes are used for the solution hydrogenation or the latex hydrogenation of nitrile rubbers.

Furthermore, the present invention also relates to a process for preparing partially or fully saturated compounds by contacting unsaturated compounds comprising at least one C═C double bond with hydrogen in the presence of at least one compound according to general formula (I).

The advantages of the novel complex catalysts according to the present invention are a surprisingly superior turn-over frequency (TOF) for NBR hydrogenation and a higher long term storage in air with moisture.

DETAILED DESCRIPTION OF THE INVENTION

The novel catalysts according to general formula (I) are excellently suited for hydrogenating a broad variety of unsaturated compounds, whether these unsaturated compounds are low molecular weight substances, oligomers or polymers. The novel complex catalysts according to general formula (I) are in particular suited for hydrogenating unsaturated polymers like nitrile rubber showing a very high hydrogenation activity so that the use of co-catalysts is no longer necessary and the amount of catalyst to be used is so low that a later removal and recycling of the catalyst may be skipped. In one embodiment of the invention nitrile rubber can be hydrogenated to more than 90% conversion, preferably to more than 95% conversion within 4 hours, preferably within 2 hours, even more preferably within 1 hour using the novel complex catalyst with an extremely low Ru metal loading of e.g. –22 ppm of Ru (corresponding to 0.015 phr of the complex catalyst).

The novel complex catalysts show a very high stability when being exposed to air or water. With regard to the hydrogenation of nitrile rubber, it was shown that the novel catalysts are very active at 100° C. or above. If nitrile rubber is hydrogenated in the presence of the novel complex catalysts, the resulting hydrogenated nitrile rubber does not show any gel formation.

The term "substituted" used for the purposes of the present patent application means that a hydrogen atom on an indicated radical or atom has been replaced by another group or moiety, with the proviso that the valency of the atom indicated is not exceeded and the substitution leads to a stable compound.

For the purposes of the present invention, all the definitions of moieties, parameters or explanations given above or below in general terms or in preferred ranges can be combined with one another in any way and shall be considered as disclosed this way, i.e. including combinations of the respective ranges and preferred ranges.

Complex Catalyst:

The invention relates to novel complexes having the general formula (I)

wherein
M represents ruthenium or osmium
X represents F, Cl, Br, I, —OH, —CF$_3$, pyridine, —OC$_6$H$_5$, —CF$_3$COO$^-$, —CH$_3$SO$_3^-$, or —BF$_4^-$,
$L^1$ represents a N-heterocyclic carbene (NHC) ligand,
$L^2$ represents a phosphine ligand,
$R^1$ represents hydrogen
$R^2$ represents
- straight chain or branched, substituted or unsubstituted $C_1$-$C_{14}$-alkyl, preferably $C_1$-$C_8$-alkyl, more preferably methyl, ethyl, n-propyl, iso-propyl, n-butyl, iso-butyl, or tert.-butyl; or
- substituted or unsubstituted $C_3$-$C_{10}$-cycloalkyl, preferably $C_5$-$C_8$-cycloalkyl, more preferably cyclopentyl, cyclohexyl or cycloheptyl; or
- substituted or unsubstituted $C_6$-$C_{14}$-aryl, preferably $C_6$-$C_{10}$-aryl, more preferably phenyl, which is either unsubstituted or comprises 1, 2, 3, 4 or 5 identical or different substituents.

In a preferred embodiment the present invention provides complexes of the general formula (I), wherein
$L^1$, $L^2$, X and $R^1$ have the same meanings as above,
$R^2$ represents

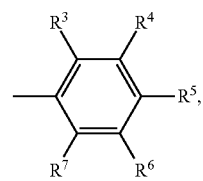

wherein
$R^3$, $R^4$, $R^5$, $R^6$ and $R^7$ are each individually of each other
- H, —NO$_2$, F, Cl, Br, I or —CN; or
- straight chain or branched, substituted or unsubstituted $C_1$-$C_{14}$-alkyl, preferably $C_1$-$C_6$-alkyl, more preferably methyl, ethyl, n-propyl, iso-propyl, n-butyl, iso-butyl, or tert.-butyl; or
- substituted or unsubstituted $C_3$-$C_{10}$-cycloalkyl, preferably $C_5$-$C_8$-cycloalkyl, more preferably cyclopentyl, cyclohexyl or cycloheptyl; or
- substituted or unsubstituted $C_8$-$C_{14}$-aryl, preferably $C_6$-$C_{10}$-aryl, more preferably phenyl, which is either unsubstituted or comprises 1, 2, 3, 4 or 5 identical or different substituents; or Pyren, Perylen, Benz(a)pyren; or
—OR$^{12}$, —OC(=O)R$^{12}$, —C(=O)OR$^{12}$, —SO$_3$R$^{12}$, —SO$_3$N(R$^{12}$)$_2$ or —SO$_3$Na wherein R$^{12}$ represents H, straight chain or branched, substituted or unsubstituted C$_1$-C$_{14}$-alkyl, preferably C$_1$-C$_8$-alkyl, more preferably methyl, ethyl, n-propyl, iso-propyl, n-butyl, iso-butyl, or tert.-butyl; or
—(N(R$^{13}$)$_3$)$^+$X$^-$ wherein X is halide, preferably chloride, and R$^{13}$ are identical or different and represent H; straight chain or branched, substituted or unsubstituted C$_1$-C$_{14}$-alkyl, preferably C$_1$-C$_8$-alkyl, more preferably methyl, ethyl, n-propyl, iso-propyl, n-butyl, iso-butyl, or tert.-butyl; substituted or unsubstituted C$_6$-C$_{14}$-aryl, preferably C$_6$-C$_{10}$-aryl, more preferably phenyl, which—is either unsubstituted or comprises 1, 2, 3, 4 or 5 Identical or different substituents; most preferably —N(CH$_3$)(C$_2$H$_5$)$_2$$^+$Cl$^-$, —N(C$_2$H$_5$)$_2$H$^+$Cl$^-$, —NH$_3^+$Cl$^-$, —NH(CH$_3$)$_2$$^+$Cl$^-$, or —N(CH$_3$)$_3$$^+$Cl$^-$; or
tris (C$_1$-C$_6$-alkoxy)silyl-C$_1$-C$_6$-alkyl, tris (C$_6$-C$_{14}$-aryloxy)silyl-C$_1$-C$_6$-alkyl, or tris (C$_3$-C$_{10}$-cycloalkoxy)silyl-C$_1$-C$_6$-alkyl, preferably trisethoxysilyl-n-propyl.

In a more preferred embodiment the present invention provides complexes of general formula (I) wherein
M represents ruthenium
L$^1$ represents IMes, SIMes, IPr or SIPr,
L$^2$ represents PCy$_3$ or PPh$_3$,
X represents Cl,
R$^1$ represents hydrogen,
R$^2$ represents

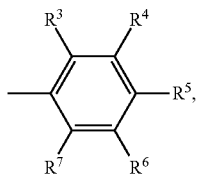

wherein
R$^3$, R$^4$, R$^5$, R$^6$ and R$^7$ are each individually of each other hydrogen, —C(=O)OCH$_3$, methoxy, ethoxy or iso-propoxy.

In an even more preferred embodiment the present invention provides complexes of general formula (I)
wherein
M represents ruthenium
L$^1$ represents IMes or SIMes
L$^2$ represents PCy$_3$,
X represents Cl,
R$^1$ represents hydrogen,
R$^2$ represents

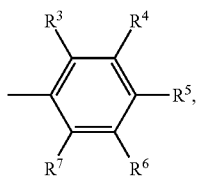

wherein
R$^3$, R$^4$, R$^5$, R$^6$ and R$^7$ are each individually of each other hydrogen, methoxy, ethoxy or iso-propoxy.

Metal M:
The metal M according to general formula (I) represents ruthenium or osmium.
In a preferred embodiment, the metal M is ruthenium.
Vinyl-ligand Residues:
The residues of the vinyl-ligand R$^1$ and R$^2$ according to general formula (I) have the following meanings:
R$^1$ represents hydrogen and
R$^2$ represents
straight chain or branched, substituted or unsubstituted C$_1$-C$_{14}$-alkyl, preferably C$_1$-C$_8$-alkyl, more preferably methyl, ethyl, n-propyl, iso-propyl, n-butyl, iso-butyl, or tert.-butyl; or
substituted or unsubstituted C$_3$-C$_{10}$-cycloalkyl, preferably C$_6$-C$_8$-cycloalkyl, more preferably cyclopentyl, cyclohexyl or cycloheptyl; or
substituted or unsubstituted C$_6$-C$_{14}$-aryl, preferably C$_5$-C$_{10}$-aryl, more preferably phenyl, which is either unsubstituted or comprises 1, 2, 3, 4 or 5 identical or different substituents.

In a preferred embodiment, the residues of the vinyl-ligand R$^1$ and R$^2$ according to general formula (I) have the following meanings:
R$^1$ represents hydrogen, and
R$^2$ represents

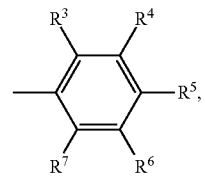

wherein
R$^3$, R$^4$, R$^5$, R$^6$ and R$^7$ are each individually of each other H, —NO$_2$, F, Cl, Br, I, —CN; or
straight chain or branched, substituted or unsubstituted C$_1$-C$_{14}$-alkyl, preferably C$_1$-C$_8$-alkyl, more preferably methyl, ethyl, n-propyl, iso-propyl, n-butyl, iso-butyl, or tert.-butyl; or
substituted or unsubstituted C$_3$-C$_{10}$-cycloalkyl, preferably C$_5$-C$_8$-cycloalkyl, more preferably cyclopentyl, cyclohexyl or cycloheptyl; or
substituted or unsubstituted C$_6$-C$_{14}$-aryl, preferably C$_6$-C$_{10}$-aryl, more preferably phenyl, which is either unsubstituted or comprises 1, 2, 3, 4 or 5 identical or different substituents; or
Pyren, Perylen, Benz(a)pyren; or
—OR$^{12}$, —OC(=O)R$^{12}$, —C(=O)OR$^{12}$, —SO$_3$R$^{12}$, —SO$_3$N(R$^{12}$)$_2$ or —SO$_3$Na wherein R$^{12}$ represents H, straight chain or branched, substituted or unsubstituted C$_1$-C$_{14}$-alkyl, preferably C$_1$-C$_8$-alkyl, more preferably methyl, ethyl, n-propyl, iso-propyl, n-butyl, iso-butyl, or tert.-butyl; or
—(N(R$^{13}$)$_3$)$^+$X$^-$ wherein X is halide, preferably chloride, and R$^{13}$ are identical or different and represent H; straight chain or branched, substituted or unsubstituted C$_1$-C$_{14}$-alkyl, preferably C$_1$-C$_8$-alkyl, more preferably methyl, ethyl, n-propyl, iso-propyl, n-butyl, iso-butyl, or tert.-butyl; substituted or unsubstituted C$_6$-C$_{14}$-aryl, preferably C$_8$-C$_{10}$-aryl, more preferably phenyl, which—is either unsubstituted or comprises 1, 2, 3, 4 or 5 identical or different substituents; most preferably —N(CH$_3$)(C$_2$H$_5$)$_2$$^+$Cl$^-$, —N(C$_2$H$_5$)$_2$H$^+$Cl$^-$, —NH$_3^+$Cl$^-$, —NH(CH$_3$)$_2$$^+$Cl$^-$, or —N(CH$_3$)$_3$$^+$Cl$^-$; or tris (C$_1$-C$_6$-alkoxy)silyl-C$_1$-C$_6$-alkyl, tris (C$_8$-C$_{14}$-aryloxy)silyl-C$_1$-C$_6$-alkyl, or tris (C$_3$-C$_{10}$-cycloalkoxy)silyl-C$_1$-C$_6$-alkyl, preferably trisethoxysilyl-n-propyl.

The general formula (I) is preferred but not limited to trans-configuration.

NHC-ligand:

In the general formula (I) the N-heterocyclic carbene ligand represents a cyclic carbene type ligand with at least one nitrogen as hetero atom being present in the ring. The ring can exhibit different substitution patterns on the ring atoms. Preferably this substitution pattern provides a certain degree of steric crowding.

In the context of this invention the N-heterocyclic carbene ligands (hereinafter referred to as "NHC-ligand(s) and depicted as "NHC" in the general formula (I)) are preferably based on imidazoline or imidazolidine moieties.

In the general formula (I) as disclosed above with the general as well as the preferred, more preferred and particularly preferred meanings of M, X, R$^1$-R$^7$ the NHC-ligand L$^1$ typically has a structure corresponding to the general formulae (IIa) to (IIg)

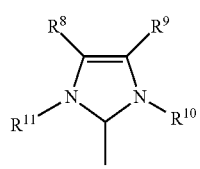
(IIa)

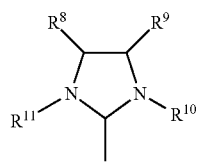
(IIb)

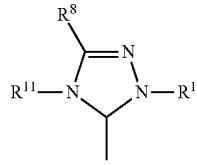
(IIc)

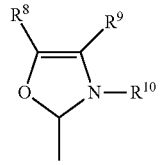
(IId)

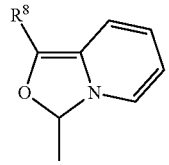
(IIe)

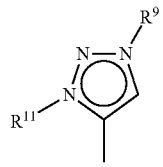
(IIf)

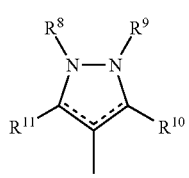
(IIg)

wherein

R$^8$, R$^9$, R$^{10}$ and R$^{11}$ are identical or different and represent hydrogen, straight-chain or branched C$_1$-C$_{30}$-alkyl, preferably methyl, ethyl, n-propyl, iso-propyl, n-butyl, iso-butyl, sec-butyl, tert-butyl, or n-pentyl, C$_3$-C$_{20}$-cycloalkyl, preferably cyclohexyl or adamantyl, C$_2$-C$_{20}$-alkenyl, C$_2$-C$_{20}$-alkynyl, C$_6$-C$_{24}$-aryl, preferably phenyl, C$_7$-C$_{25}$-alkaryl, preferably 2,4,6-trimethylphenyl (Mes) or 2,4,6-triisopropylphenyl (Trip), C$_2$-C$_{20}$-heteroaryl, C$_2$-C$_{20}$-heterocyclyl, C$_1$-C$_{20}$-alkoxy, C$_2$-C$_{20}$-alkenyloxy, C$_2$-C$_{20}$-alkynyloxy, C$_8$-C$_{20}$-aryloxy, C$_2$-C$_{20}$-alkoxycarbonyl, C$_3$-C$_{20}$-alkylthio, C$_6$-C$_{20}$-arylthio, —Si(R)$_3$, —O—Si(R)$_3$, —O—C(=O)R, C(=O)R, —C(=O)N(R)$_2$, —NR—C(=O)—N(R)$_2$, —SO$_2$N(R)$_2$, —S(=O)R, —S(=O)$_2$R, —O—S(=O)$_2$R, halogen, nitro or cyano; wherein in all directly above occurrences relating to the meanings of R$^8$, R$^9$, R$^{10}$ and R$^{11}$ the group R is identical or different and represents hydrogen, C$_1$-C$_{30}$-alkyl, C$_3$-C$_{20}$-cycloalkyl, C$_2$-C$_{20}$-alkenyl, C$_2$-C$_{20}$-alkynyl, C$_6$-C$_{24}$-aryl, or C$_2$-C$_{20}$-heteroaryl.

In these formulae (IIa) to (IIg) the carbon atom bonding to the ruthenium or osmium metal center is formally a carbene carbon.

If appropriate, one or more of R$^8$, R$^9$, R$^{10}$, and R$^{11}$ can independently of one another, be substituted by one or more substituents, preferably straight-chain or branched C$_1$-C$_{10}$-alkyl, C$_3$-C$_8$-cycloalkyl, C$_1$-C$_{10}$-alkoxy, C$_6$-C$_{24}$-aryl, C$_2$-C$_{20}$-heteroaryl, C$_2$-C$_{20}$-heterocyclyl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein the abovementioned substituents, to the extent chemically possible, may in turn be substituted by one or more substituents, preferably selected from the group consisting of halogen, in particular chlorine or bromine, C$_1$-C$_5$-alkyl, C$_1$-C$_5$-alkoxy and phenyl.

Merely for the sake of clarity, it may be added that the structures of the NHC-ligand depicted in the general formulae (IIa) and (IIb) in the present patent application are equivalent to the structures (IIa-(i)) and (IIb-(i)) which are frequently also found in the literature for such NHC-ligands, respectively, and emphasize the carbene character of the NHC-ligand. This applies analogously to the further structures (IIc) to (IIe) as well as the associated preferred structures (IIIa)-(IIIu) depicted below.

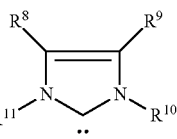
(IIa-(i))

-continued (IIb-(i))

In preferred NHC-ligand(s) in the catalysts of the general formula (I)

$R^8$ and $R^9$ are identical or different and represent hydrogen, $C_6$-$C_{24}$-aryl, more preferably phenyl, straight-chain or branched $C_1$-$C_{10}$-alkyl, more preferably methyl, ethyl, n-propyl, iso-propyl, n-butyl, sec-butyl, iso-butyl or tert.-butyl or form a cycloalkyl or aryl structure together with the carbon atoms to which they are bound.

The preferred and more preferred meanings of $R^8$ and $R^9$ may be either unsubstituted or substituted by one or more further substituents selected from the group consisting of straight-chain or branched $C_1$-$C_{10}$-alkyl or $C_1$-$C_{10}$-alkoxy, $C_3$-$C_8$-cycloalkyl, $C_6$-$C_{24}$-aryl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein all these substituents may in turn be either unsubstituted or substituted by one or more substituents, preferably selected from the group consisting of halogen, in particular chlorine or bromine, $C_1$-$C_5$-alkyl, $C_1$-$C_5$-alkoxy and phenyl.

In further preferred NHC-ligand(s) in the catalysts of the general formula (I)

$R^{10}$ and $R^{11}$ are identical or different and preferably represent straight-chain or branched $C_1$-$C_{10}$-alkyl, more preferably iso-propyl or n-pentyl, $C_3$-$C_{10}$-cycloalkyl, more preferably adamantyl, substituted or unsubstituted $C_6$-$C_{24}$-aryl, more preferably phenyl, 2,6-diisopropylphenyl, 2,6-dimethylphenyl, or 2,4,6-trimethylphenyl, $C_1$-$C_{10}$-alkylsulfonate, or $C_8$-$C_{10}$-arylsulfonate.

These preferred meanings of $R^{10}$ and $R^{11}$ may be either unsubstituted or substituted by one or more further substituents selected from the group consisting of straight-chain or branched $C_1$-$C_{10}$-acyl or $C_1$-$C_{10}$-alkoxy, $C_3$-$C_8$-cycloalkyl, $C_5$-$C_{24}$-aryl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein all these substituents may in turn be either unsubstituted or substituted by one or more substituents, preferably selected from the group consisting of halogen, in particular chlorine or bromine, $C_1$-$C_5$-alkyl, $C_1$-$C_5$-alkoxy and phenyl.

In further preferred NHC-ligand(s) in the catalysts of the general formula (I)

$R^8$ and $R^9$ are identical or different and represent hydrogen, $C_5$-$C_{24}$-aryl, more preferably phenyl, straight-chain or branched $C_1$-$C_{10}$-alkyl, more preferably methyl, ethyl, n-propyl, iso-propyl, n-butyl, sec-butyl, and iso-butyl, or form a cycloalkyl or aryl structure together with the carbon atoms to which they are bound, and $R^{10}$ and $R^{11}$ are identical or different and preferably represent straight-chain or branched $C_1$-$C_{10}$-alkyl, more preferably iso-propyl or n-pentyl, $C_3$-$C_{10}$-cycloalkyl, more preferably adamantyl, substituted or unsubstituted $C_6$-$C_{24}$-aryl, more preferably phenyl, 2,6-diisopropylphenyl, 2,6-dimethylphenyl, 2,4,6-trimethylphenyl, $C_1$-$C_{10}$-alkylsulfonate, or $C_8$-$C_{10}$-arylsulfonate, wherein all such meanings of $R^8$, $R^9$, $R^{10}$ and $R^{11}$ can be unsubstituted or substituted with the same substitution pattern as outlined above with respect to the $R^8$ and $R^9$, on the one hand, and $R^{10}$ and $R^{11}$, on the other hand.

Particularly preferred NHC-ligands have the following structures (IIIa) to (IIIu), where "Ph" stands in each case for phenyl, "Bu" stands in each case for butyl, i.e. either n-butyl, sec.-butyl, iso-butyl or tert.-butyl, "Mes" stands in each case for 2,4,6-trimethylphenyl, "Dipp" stands in al cases for 2,6-diisopropylphenyl and "Dimp" stands in each case for 2,6-dimethylphenyl.

(IIIa)

(IIIb)

(IIIc)

(IIId)

(IIIe)

(IIIf)

(IIIg)

(IIIh)

(IIIj)

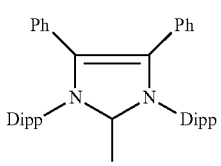
(IIIk)

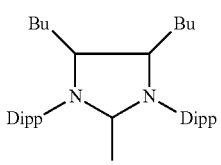
(IIIm)

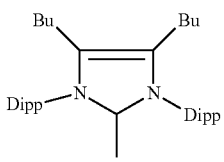
(IIIn)

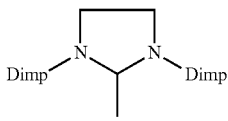
(IIIp)

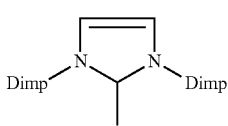
(IIIq)

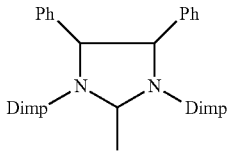
(IIIr)

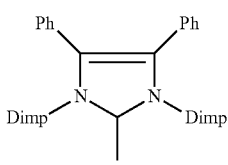
(IIIs)

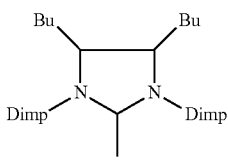
(IIIt)

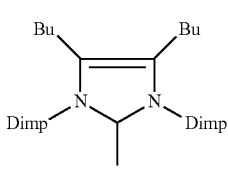
(IIIu)

Where the NHC-ligand comprises not only an "N" (nitrogen), but also an "O" (oxygen) in the ring it is preferred that the substitution pattern of $R^8$, $R^9$, $R^{10}$ and/or $R^{11}$ provides a certain steric crowding.

$L^2$ (Phosphine Ligand):

In the general formula (I), the ligand $L^2$ represents a phosphine ligand.

Preferred ligands $L^2$ are bulky phosphine ligands such as di-tert.-butylalkyl-, tricyclohexyl-, triaryl- or tri-isopropyl-phosphines.

More preferred ligands $L^2$ are cycloalkyl phosphines or aryl phosphines.

X Ligand:

In the present invention, X represents F, Cl, Br, I, —OH, —CF$_3$, pyridine, —OC$_6$H$_5$, —CF$_3$COO$^-$, —CH$_3$SO$_3^-$, or —BF$_4^-$, more preferably F, Cl, Br and even more preferably Cl. In case that the ligand has a negative charge, the counterion can be typically of any type, eg. H+, alkaline metal cations or organic cations.

Process for Preparing the Ruthenium or Osmium-based Complexes of General Formula (I)

The novel highly active catalysts can be synthesized starting from commercially available raw materials such as e.g. RuH(CO)Cl(PCy$_3$)$_2$, as possible pathway:

The compounds of general formula (I) can be prepared by reacting a compound of general formula (1)

(1)

wherein

M represents ruthenium or osmium,
X represents F, Cl, Br, I, —OH, —CF$_3$, pyridine, —OC$_6$H$_5$, —CF$_3$COO$^-$, —CH$_3$SO$_3^-$, or —BF$_4^-$,
$L^1$ represents a N-heterocyclic carbene ligand,
$L^2$ represents a phosphine ligand,
with a compound of general formula (2)

$$R^1\text{—C}\equiv\text{C—}R^2 \qquad (2)$$

wherein
$R^1$ represents hydrogen and
$R^2$ represents straight chain or branched, substituted or unsubstituted $C_1$-$C_{14}$-alkyl, preferably $C_1$-$C_8$-alkyl, more preferably methyl, ethyl, n-propyl, iso-propyl, n-butyl, iso-butyl, or tert.-butyl; or substituted or unsubstituted $C_3$-$C_{10}$-cycloalkyl, preferably $C_5$-$C_8$-cycloakyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, which aryl group, more preferably phenyl is either unsubstituted or comprises 1, 2, 3, 4 or 5 identical or different substituents.

Preferred Embodiments of the Process:

In a preferred embodiment of the process the compounds of general formula (I) can be prepared by reacting a compound of general formula (1)

wherein
M represents ruthenium or osmium,
X represents F, Cl, Br, I, —OH, —CF$_3$, pyridine, —OC$_6$H$_5$, —CF$_3$COO$^-$, —CH$_3$SO$_3^-$, or —BF$_4^-$,
$L^1$ represents a N-heterocyclic carbene ligand,
$L^2$ represents a phosphine ligand,
with a compound of general formula (2)
wherein
$R^1$ represents hydrogen and
$R^2$ represents

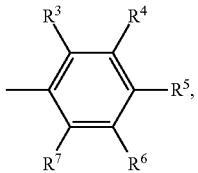

wherein

R³, R⁴, R⁵, R⁶ and R⁷ are each individually of each other
H, —NO₂, F, Cl, Br, I or —CN; or
straight chain or branched, substituted or unsubstituted C₁-C₁₄-alkyl, preferably C₁-C₈-alkyl, more preferably methyl, ethyl, n-propyl, iso-propyl, n-butyl, iso-butyl, or tert.-butyl; or
substituted or unsubstituted C₃-C₁₀-cycloalkyl, preferably C₅-C₆-cycloalkyl, more preferably cyclopentyl, cyclohexyl or cycloheptyl; or
substituted or unsubstituted C₆-C₁₄-aryl, preferably C₆-C₁₀-aryl, more preferably phenyl, which is either unsubstituted or comprises 1, 2, 3, 4 or 5 identical or different substituents; or
Pyren, Perylen, Benz(a)pyren; or
—OR¹², —OC(=O)R¹², —C(=O)OR¹², —SO₃R¹², —SO₃N(R¹²)₂ or —SO₃Na wherein R¹² represents H, straight chain or branched, substituted or unsubstituted C₁-C₁₄-alkyl, preferably C₁-C₈-alkyl, more preferably methyl, ethyl, n-propyl, iso-propyl, n-butyl, iso-butyl, or tert.-butyl; or
—(N(R¹³)₃)⁺X⁻ wherein X is halide, preferably chloride, and R¹³ are identical or different and represent H; straight chain, substituted or unsubstituted C₁-C₁₄-alkyl, preferably C₁-C₈-alkyl, more preferably methyl, ethyl, n-propyl, iso-propyl, n-butyl, iso-butyl, or tert-butyl; substituted or unsubstituted C₈-C₁₄-aryl, preferably C₆-C₁₀-aryl, more preferably phenyl, which is either unsubstituted or comprises 1, 2, 3, 4 or 5 identical or different substituents; most preferably —N(CH₃)(C₂H₅)₂⁺Cl⁻, —N(C₂H₅)₂H⁺Cl⁻, —NH₃⁺Cl⁻, —NH(CH₃)₂⁺Cl⁻, or —N(CH₃)₃⁺Cl⁻; or
tris (C₁-C₆-alkoxy)silyl-C₁-C₆-alkyl, tris(C₆-C₁₄-aryloxy)silyl-C₁-C₆-alkyl, or tris (C₃-C₁₀-cycloalkoxy)silyl-C₁-C₆-alkyl, preferably trisethoxysilyl-n-propy.

In a more preferred embodiment of the process the compounds of general formula (I) can be prepared by reacting a compound of general formula (1)
wherein
M represents ruthenium,
X represents Cl,
L¹ represents an IMes, SIMes, IPr or SIPr,
L² represents PCy₃ or PPh₃,
with a compound of general formula (2)
wherein
R¹ represents hydrogen and
R² represents

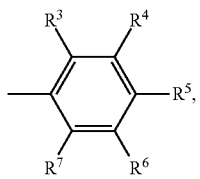

wherein
R³, R⁴, R⁵, R⁶ and R⁷ are each individually of each other represents hydrogen, —C(=O)OCH₃, methoxy, ethoxy or iso-propoxy, Further Typical Reaction Parameters:

The process is typically performed in one or more organic solvents, preferably selected from the group consisting of
ethers, more preferably THF, dioxane, and diethylether,
alkanes, more preferably hexane,
aromatic solvents, more preferably toluene, and benzene,
halogenated hydrocarbons, more preferably chloroform and chlorobenzene,
ester, more preferably ethyl acetate,
ketone, more preferably methyl ethyl ketone or acetone, and
alcohols, more preferably methanol, ethanol and methyloxyethanol.

The solvents are used pure, whereas pure means with a content of impurities of less than 1 wt.-%, more preferably free of impurities. The solvent is particularly preferred free of any other catalysts or co-catalysts.

Typical and Preferred Compounds (1):

Compound (1) is typically either commercially available or can be synthesized according to processes known to a person skilled in the art (e.g. WO-A-2013/159365).

Preferably the following compounds of general formula (1) can be used:

(1.a) RuHCl(CO)(IMes)(PCy₃), (1.b) RuHCl(CO)(SIMes)(PCy₃), (1.c) RuHCl(CO)(IPr)(PCy₃), (1.d) RuHCl(CO)(SIPr)(PCy₃), (1.e) RuHCl(CO)(IMes)(PPh₃), (1.f) RuHCl(CO)(SIMes)(PPh₃), (1.g) RuHCl(CO)(IPr)PPh₃), or (1.h) RuHCl(CO)(SIPr)(PPh₃).

Typical and Preferred Compounds (2):

Compounds of general formula (2) represent alkynes which can be easily prepared. Such preparation is well known in the art.

Preferred examples of the compounds of general formula (2) are the following:

(2.a) phenyl acetylene,
(2.b) 1-Ethynyl-2-isopropoxybenzene
(2.c) 1-Ethynyl-3-isopropoxybenzene
(2.d) 2-Ethynylanisole
(2.e) 3-Ethynylanisole
(2.f) 4-Ethynylanisole
(2.g) 1-Ethynyl-3,5-dimethoxybenzene
(2.h) Dimethyl-5-ethynylisophthalate

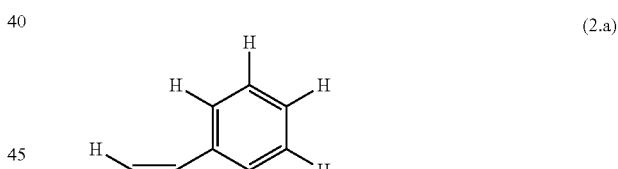
(2.a)

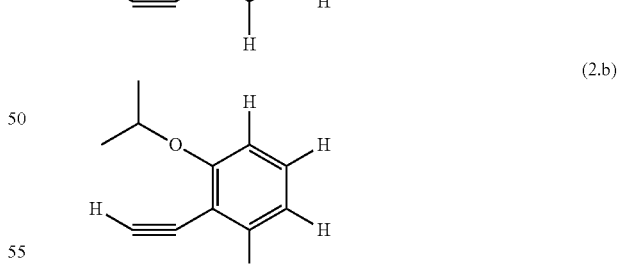
(2.b)

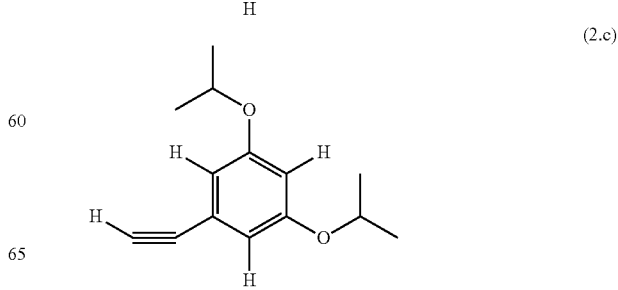
(2.c)

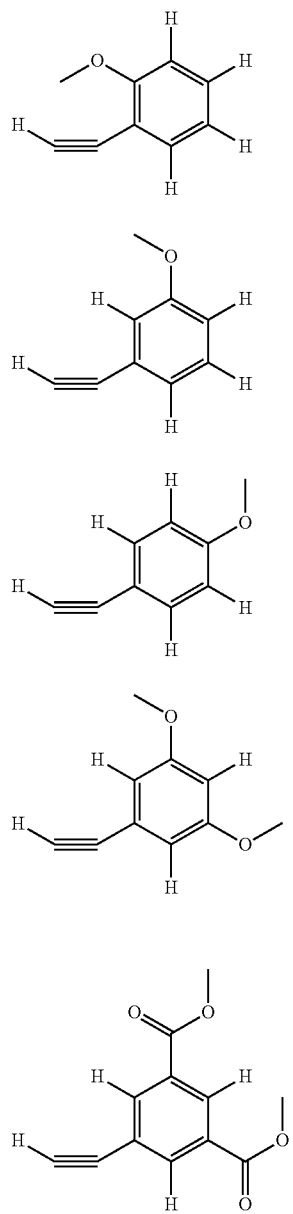

(2.d)

(2.e)

(2.f)

(2.g)

(2.h)

Typical and Preferred Complexes of General Formula (I)

The following preferred complexes falling under general formula (I) can be obtained when the following N-heterocyclic carbenes are used:

"IMes" which stands for N,N'-bis(mesityl)imidazol-2-ylidene,

"SIMes" which stands for N,N'-bis(mesityl)imidazolidin-2-ylidene,

"IPr" which stands for N,N'-bis(2,6-diisopropylphenyl)imidazol-2-ylidene,

"SIPr" which stands for N,N'-bis(2,6-diisopropylphenyl)imidazolidin-2-ylidene,

"ItBu" which stands for N,N'-bis(tert-butyl)imidazol-2-ylidene

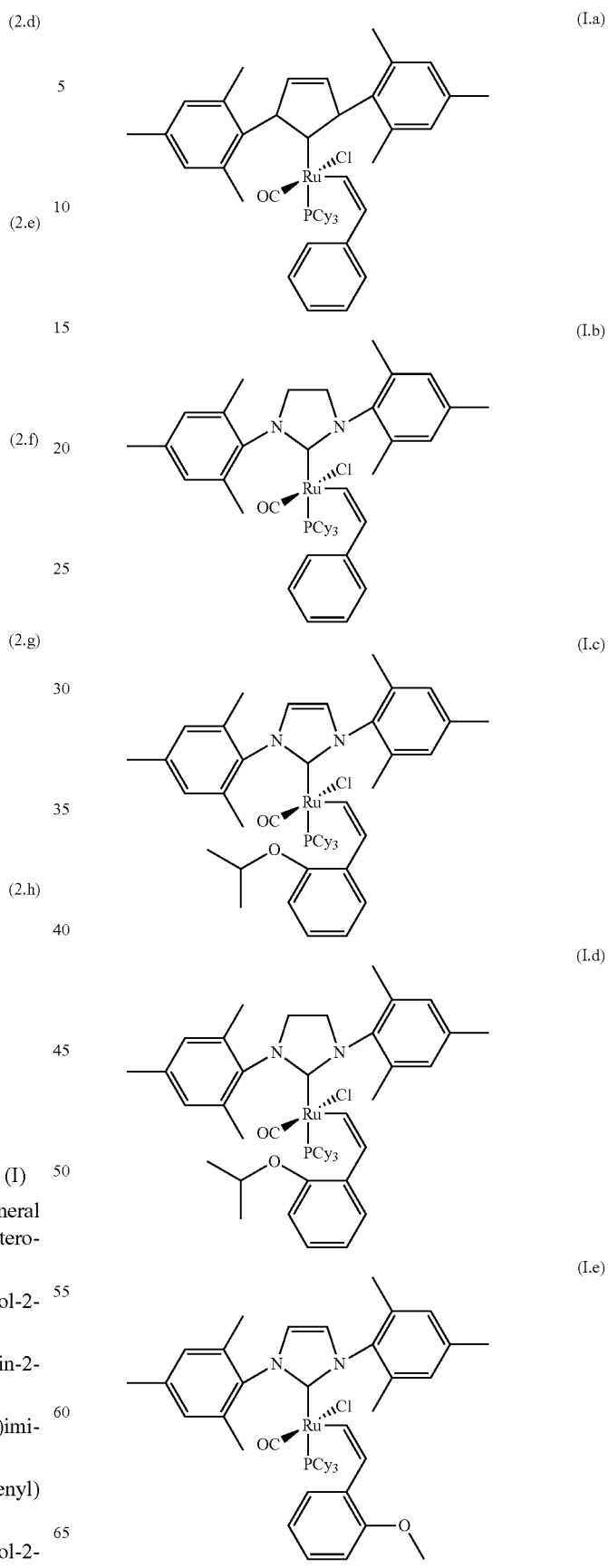

-continued
(I.f)
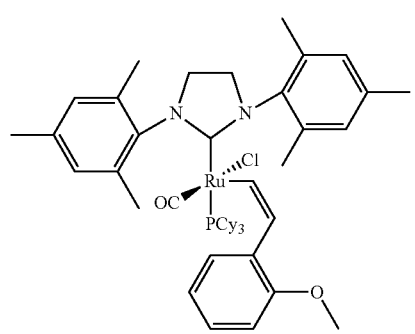
(I.g)
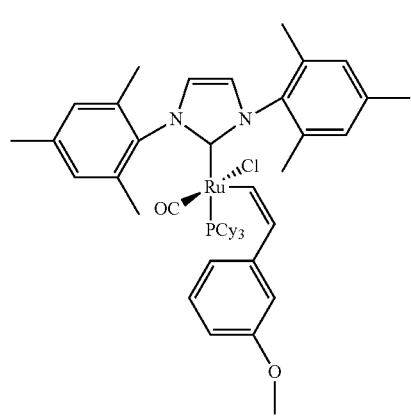
(I.h)
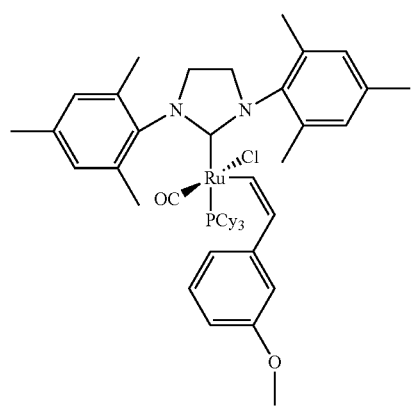
(I.i)
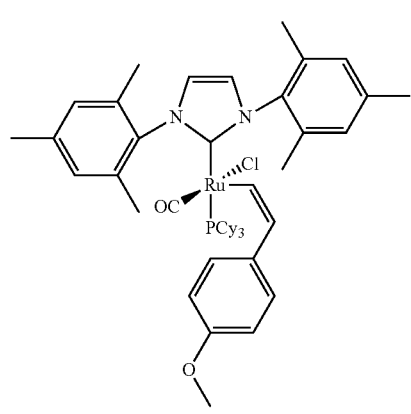
(I.j)
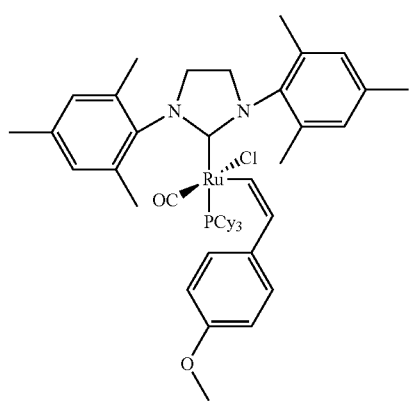
(I.k)
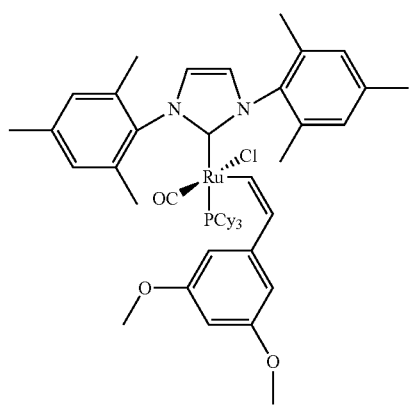
(I.l)
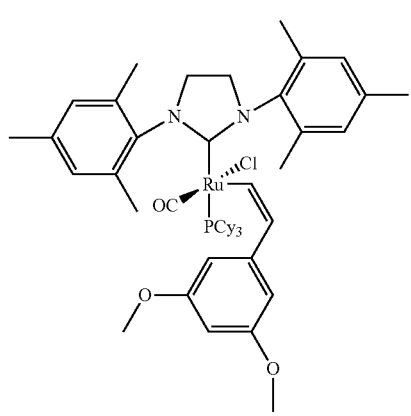
(I.m)
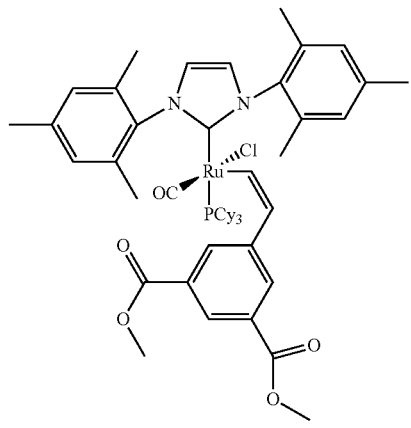

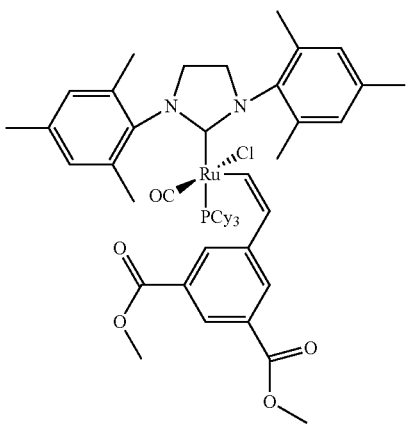

(I.n)

For the purposes of the present patent application and invention, all the definitions of radicals, parameters or explanations given above or below in general terms or in preferred ranges can be combined with one another in any way, i.e. including combinations of the respective ranges and preferred ranges.

Use of the Complexes and Process for Preparing Hydrogenated Compounds:

The novel ruthenium- or osmium-based complexes of general formula (I) are useful as catalysts, either alone or in combination with suitable co-catalysts or additives, for the hydrogenation of a wide variety of unsaturated organic and polymeric materials. However, it has been proven it is not necessary to add any co-catalysts or additives.

Hence the present invention relates to the use of the complexes of general formula (I) as catalysts for hydrogenation reactions. The present invention also relates to a process for preparing partially or fully saturated compounds by contacting unsaturated compounds comprising at least one C=C double bond with hydrogen in the presence of at least one compound according to general formula (I).

Substrates to be Hydrogenated:

The process of the present invention is broadly applicable to the hydrogenation of a variety of substrates, including terminal olefins, internal olefins, cyclic olefins, conjugated olefins, and any further olefins having at least one carbon-carbon double bond and additionally at least one further polar unsaturated double or triple bond. The process is also applicable to the hydrogenation of polymers having carbon-carbon double bonds. Such polymers may represent homo-, co-, ter- or quaterpolymers.

As a terminal olefin or alkene, it is possible to hydrogenate a hydrocarbon compound with a terminal unsaturated carbon-carbon double bond having the general formula $C_nH_{2n}$. The terminal olefin can be a straight-chain or a branched hydrocarbon compound of any length, preferably 1-hexene.

As an internal olefin or alkene, it is possible to hydrogenate a hydrocarbon compound with an internal unsaturated carbon-carbon double bond having the general formula $C_nH_{2n}$. The internal olefin can be a straight-chain or a branched hydrocarbon of any length, preferably 2-hexene.

As a cyclic olefin or cycloalkene, it is possible to hydrogenate a hydrocarbon compound with a cyclic unsaturated carbon-carbon double bond having the general formula $C_nH_{2n-2}$. The cyclic olefin can be a ring of any size, preferably cyclohexene.

As a conjugated olefin or dialkene, it is possible to hydrogenate a hydrocarbon compound with conjugated carbon-carbon unsaturated double bonds. The conjugation can be a straight-chain or a branched hydrocarbon of any length, preferably styrene.

As an olefin, it is also possible to selectively hydrogenate a hydrocarbon compound with at least one unsaturated carbon-carbon double bond and least one other unsaturated polar double or triple bond. Such unsaturated polar bonds are surprisingly left unaltered. The carbon-carbon double bond in such olefins can be of any nature including terminal, internal, cyclic and conjugated ones. The additional unsaturated polar bond can be of any nature with preference given to carbon-nitrogen, carbon-phosphorus, carbon-oxygen, and carbon-sulfur unsaturated polar bonds.

Polymers having carbon-carbon double bonds may also be subjected to the inventive process. Such polymers preferably comprise repeating units based on at least one conjugated diene monomer.

The conjugated diene can be of any nature. In one embodiment ($C_4$-$C_6$) conjugated dienes are used. Preference is given to 1,3-butadiene, isoprene, 1-methylbutadiene, 2,3-dimethyl-butadiene, piperylene, chloroprene, or mixtures thereof. More preference is given to 1,3-butadiene, isoprene or mixtures thereof. Particular preference is given to 1,3-butadiene.

In a further embodiment polymers having carbon-carbon double bonds may be subjected to the inventive process which comprise repeating units of not only at least one conjugated diene as monomer (a) but additionally at least one further copolymerizable monomer (b).

Examples of suitable monomers (b) are olefins, such as ethylene or propylene.

Further examples of suitable monomers (b) are vinylaromatic monomers, like styrene, α-methyl styrene, o-chlorostyrene or vinyltoluenes, vinylesters of aliphatic or branched $C_1$-$C_{18}$ monocarboxylic acids, such as vinyl acetate, vinyl propionate, vinyl butyrate, vinyl valerate, vinyl hexanoate, vinyl 2-ethylhexanoate, vinyl decanoate, vinyl laurate and vinyl stearate.

A preferred polymer to be used in the present invention is a copolymer of 1,3-butadiene and styrene or alpha-methylstyrene. Said copolymers may have a random or block type structure.

Further examples of suitable monomers (b) are esters of ethylenically unsaturated monocarboxylic acids or mono- or diesters of dicarboxylic acids with generally $C_1$-$C_{12}$ alkanols, e.g. esters of acrylic acid, methacrylic acid, maleic acid, fumaric acid and itaconic acid with e.g. methanol, ethanol, n-propanol, isopropanol, 1-butanol, 2-butanol, isobutanol, tert.-butanol, n-hexanol, 2-ethylhexanol, or $C_5$-$C_{10}$-cycloalkanols, such as cyclopentanol or cyclohexanol, and of these preferably the esters of acrylic and/or methacrylic acid, examples being methyl methacrylate, n-butyl methacrylate, tert-butyl methacrylate, n-butyl acrylate, tert-butyl acrylate, and 2-ethylhexyl acrylate.

Nitrile Rubber:

The inventive process may be further used to hydrogenate so-called nitrile rubbers. Nitrile rubbers (also abbreviated as "NBR") represent copolymers or terpolymers comprising repeating units of at least one conjugated diene, at least one α,β-unsaturated nitrile monomer and, if appropriate, one or more further copolymerizable monomers.

The conjugated diene can be of any nature. Preference is given to using ($C_4$-$C_6$) conjugated dienes, more preferably selected from the group consisting of 1,3-butadiene, isoprene, 2,3-dimethylbutadiene, piperylene and mixtures thereof. Very particular preference is given to 1,3-butadiene and isoprene or mixtures thereof. Especial preference is given to 1,3-butadiene.

As α,β-unsaturated nitrite, it is possible to use any known α,β-unsaturated nitrite, preferably a ($C_3$-$C_5$) α,β-unsaturated nitrile, more preferably selected from the group consisting of acrylonitrile, methacrylonitrile, ethacrylonitrile and mixtures thereof. Particular preference is given to acrylonitrile.

A particularly preferred nitrile rubber used in the process of this invention is thus a copolymer having repeating units derived from acrylonitrile and 1,3-butadiene.

Apart from the conjugated diene and the α,β-unsaturated nitrile, the nitrile rubber may comprise repeating units of one or more further copolymerizable monomers known in the art, e.g. α,β-unsaturated (preferably mono-unsaturated) monocarboxylic acids, their esters and amides, α,β-unsaturated (preferably mono-unsaturated) dicarboxylic acids, their mono- or diesters, as well as the respective anhydrides or amides of said α,β-unsaturated dicarboxylic acids.

As α,β-unsaturated monocarboxylic acids acrylic acid and methacrylic acid are preferably used.

Esters of α,β-unsaturated monocarboxylic acids may also be used, in particular alkyl esters, alkoxyalkyl esters, aryl esters, cycloalkylesters, cyanoalkyl esters, hydroxyalkyl esters, and fluoroalkyl esters.

As alkyl esters $C_1$-$C_{16}$ alkyl esters of the α,β-unsaturated monocarboxylic acids are preferably used, more preferably $C_1$-$C_{18}$ alkyl esters of acrylic acid or methacrylic acid, such as methylacrylate, ethylacrylate, propylacrylate, n-butylacrylate, tert.-butylacrylate, 2-ethyl-hexylacrylate, n-dodecylacrylate, methylmethacrylate, ethylmethacrylate, propylmethacrylate, n-butylmethacrylate, tert.-butylmethacrylate and 2-ethylhexyl-methacrylate.

As alkoxyalkyl esters $C_2$-$C_{18}$ alkoxyalkyl esters of α,β-unsaturated monocarboxylic acids are preferably used, more preferably alkoxyalkylester of acrylic acid or methacrylic acid such as methoxy methyl(meth)acrylate, methoxy ethyl(meth)acrylate, ethoxyethyl(meth)acrylate and methoxyethyl(meth)acylate.

It is also possible to use aryl esters, preferably $C_5$-$C_{14}$-aryl-, more preferably $C_6$-$C_{10}$-aryl esters and most preferably the aforementioned aryl esters of acrylates and methacrylates.

In another embodiment cycloalkyl esters, preferably $C_5$-$C_{12}$-, more preferably $C_6$-$C_{12}$-cyclo-alkyl and most preferably the aforementioned cycloalkyl acrylates and methacrylates are used.

It is also possible to use cyanoalkyl esters, in particular cyanoalkyl acrylates or cyanoalkyl methacrylates, with 2 to 12 C atoms in the cyanoalkyl group, preferably α-cyanoethyl acrylate, β-cyanoethyl acrylate or cyanobutyl methacrylate.

In another embodiment hydroxyalkyl esters are used, in particular hydroxyalkyl acrylates and hydroxyalkyl methacrylates with 1 to 12 C-atoms in the hydroxylalkyl group, preferably 2-hydroxyethyl acrylate, 2-hydroxyethyl methacrylate or 3-hydroxypropyl acrylate.

It is also possible to use fluorobenzyl esters, in particular fluorobenzyl acrylates or fluorobenzyl methacrylates, preferably trifluoroethyl acrylate and tetrafluoropropyl methacrylate. Substituted amino group containing acrylates and methacrylates may also be used like dimethylaminomethyl acrylate and diethylaminoethylacrylate.

Various other esters of the α,β-unsaturated carboxylic acids may also be used, like e.g. polyethyleneglycol(meth)acrylate, polypropyleneglycole(meth)acrylate, glycidyl (meth)acrylate, epoxy(meth)acrylate, N-(2-hydroxyethyl) acrylamide, N-(2-hydroxymethyl) acrylamide or urethane (meth)acrylate.

It is also possible to use mixture of all aforementioned esters of α,β-unsaturated carboxylic acids.

Further on α,β-unsaturated dicarboxylic acids may be used, preferably maleic acid, fumaric acid, crotonic acid, itaconic acid, citraconic acid and mesaconic acid.

In another embodiment anhydrides of α,β-unsaturated dicarboxylic acids are used, preferably maleic anhydride, itaconic anhydride, itaconic anhydride, citraconic anhydride and mesaconic anhydride.

In a further embodiment mono- or diesters of α,β-unsaturated dicarboxylic acids can be used. Suitable alkyl esters are e.g. $C_1$-$C_{10}$-alkyl, preferably ethyl-, n-propyl-, iso-propyl, n-butyl-, tert.-butyl, n-pentyl- or n-hexyl mono- or diesters. Suitable alkoxyalkyl esters are $C_2$-$C_{12}$-alkoxyalkyl-, preferably $C_3$-$C_8$-alkoxyalkyl mono- or diesters. Suitable hydroxyalkyl esters are $C_1$-$C_{12}$ hydroxyalkyl-, preferably $C_2$-$C_8$-hydroxyalkyl mono- or diesters. Suitable cycloalkyl esters are $C_5$-$C_{12}$-cycloakyl-, preferably $C_6$-$C_{12}$-cycloakyl mono- or diesters. Suitable alkylcycloalkyl esters are $C_6$-$C_{12}$-alkylcycloalkyl-, preferably $C_7$-$C_{10}$-alkylcycloalkyl mono- or diesters. Suitable aryl esters are $C_6$-$C_{14}$-aryl, preferably $C_6$-$C_{10}$-aryl mono- or diesters.

Explicit examples of the α,β-ethylenically unsaturated dicarboxylic acid monoester monomers include maleic acid monoalkyl esters, preferably monomethyl maleate, monoethyl maleate, monopropyl maleate, and mono n-butyl maleate;

maleic acid monocycloalkyl esters, preferably monocyclopentyl maleate, monocyclohexyl maleate, and monocycloheptyl maleate;

maleic acid monoalkylcycloalkyl esters, preferably monomethylcyclopentyl maleate, and monoethylcyclohexyl maleate;

maleic acid monoaryl ester, preferably monophenyl maleate;

maleic acid mono benzyl ester, preferably monobenzyl maleate;

fumaric acid monoalkyl esters, preferably monomethyl fumarate, monoethyl fumarate, monopropyl fumarate, and mono n-butyl fumarate;

fumaric acid monocycloalkyl esters, preferably monocyclopentyl fumarate, monocycohexyl fumarate, and monocycloheptyl fumarate;

fumaric acid monoalkylcycloalkyl esters, preferably monomethylcyclopentyl fumarate, and monoethylcyclohexyl fumarate;

fumaric acid monoaryl ester, preferably monophenyl fumarate;

fumaric acid mono benzyl ester, preferably monobenzyl fumarate;

citraconic acid monoalkyl esters, preferably monomethyl citraconate, monoethyl citraconate, monopropyl citraconate, and mono n-butyl citraconate;

citraconic acid monocycloalkyl esters, preferably monocyclopentyl citraconate, monocyclohexyl citraconate, and monocycloheptyl citraconate;

citraconic acid monoalkylcycloalkyl esters, preferably monomethylcyclopentyl citraconate, and monoethylcyclohexyl citraconate;

citraconic acid mono aryl ester, preferably monophenyl citraconate;

citraconic acid mono benzyl ester, preferably monobenzyl citraconate;

itaconic acid mono alkyl esters, preferably monomethyl itaconate, monoethyl itaconate, monopropyl itaconate, and mono n-butyl itaconate;

itaconic acid monocycloalkyl esters, preferably monocyclopentyl itaconate, monocyclohexyl itaconate, and monocycloheptyl itaconate;

itaconic acid monoalkylcycloalkyl esters, preferably monomethylcyclopentyl itaconate, and monoethylcyclohexyl itaconate;

itaconic acid mono aryl ester, preferably monophenyl itaconate;

itaconic acid mono benzyl ester, preferably monobenzyl itaconate.

As α,β-ethylenically unsaturated dicarboxylic acid diester monomers the analogous diesters based on the above explicitly mentioned mono ester monomers may be used, wherein, however, the two organic groups linked to the C=O group via the oxygen atom may be identical or different.

As further termonomers vinyl aromatic monomer like styrol, α-methylstyrol and vinylpyridine, as well as non-conjugated dienes like 4-cyanocyclohexene and 4-vinylcyclohexene, as well as alkynes like 1- or 2-butyne may be used.

Particularly preferred are termonomers chosen from the below depicted formulae:

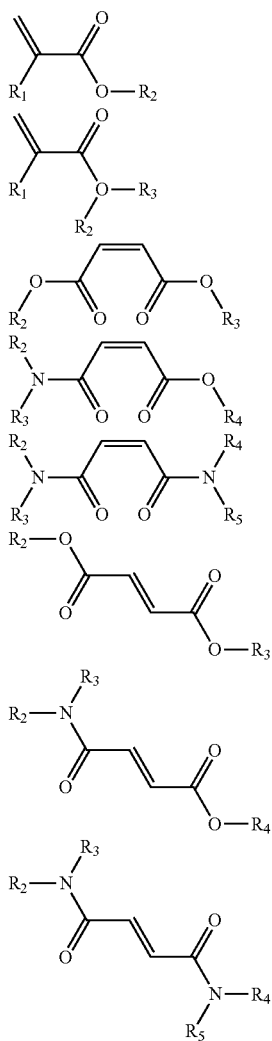
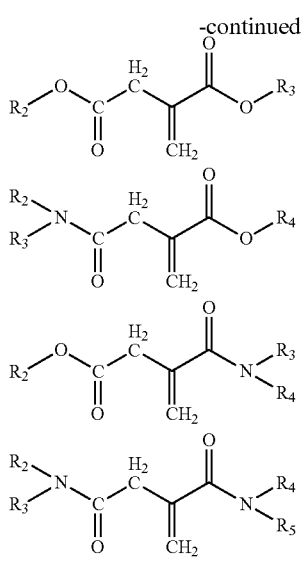

wherein
$R_1$ is hydrogen or a methyl group, and
$R_2$, $R_3$, $R_4$, $R_5$ are identical or different and may represent H, $C_1$-$C_{12}$ alkyl, $C_3$-$C_8$ cycloalkyl, alkoxyalkyl, hydroxyalkyl, epoxyalkyl, aryl, or heteroaryl.

The proportions of conjugated diene and α,β-unsaturated nitrile in the NBR polymers to be used can vary within wide ranges. The proportion of the conjugated diene or the sum of conjugated dienes is usually in the range from 40 to 90% by weight, preferably in the range from 60 to 85% by weight, based on the total polymer. The proportion of α,β-unsaturated nitrile or the sum of α,β-unsaturated nitriles is usually from 10 to 60% by weight, preferably from 15 to 40% by weight, based on the total polymer. The proportions of the monomers in each case add up to 100% by weight. The additional monomers can be present in amounts of from 0 to 40% by weight, preferably from 0.1 to 40% by weight, particularly preferably from 1 to 30% by weight, based on the total polymer. In this case, corresponding proportions of the conjugated diene or dienes and/or the α,β-unsaturated nitrile or nitriles are replaced by proportions of the additional monomers, with the proportions of all monomers in each case adding up to 100% by weight.

The preparation of the nitrile rubbers by polymerization of the abovementioned monomers is adequately and comprehensively known from prior art. Nitrile rubbers which can be used for the purposes of the invention are also commercially available, e.g. as products from the product range of the Perbunan® and Krynac® grades of Lanxess Deutschland GmbH.

Process Conditions for Hydrogenating the Unsaturated Substrates:

The hydrogenation of the unsaturated substrates, in particular the nitrile rubber can be carried out by bringing the unsaturated substrates, in particular the nitrile rubber, into contact with the novel complex catalyst of general formula (I) in the presence of hydrogen gas.

The hydrogenation is preferably carried out at a temperature in the range of from 30° C. to 200° C., preferably from 40° C. to 180° C., more preferably from 50° C. to 160° C., most preferably from 100° C. to 150° C. and at a hydrogen pressure in the range of 0.5 MPa to 35 MPa, more preferably of 3.0 MPa to 10 MPa.

Preferably, the hydrogenation time is from 10 minutes to 48 hours, preferably from 15 minutes to 24 hours, more preferably from 30 minutes to 4 hours, even more preferably from 1 hour to 8 hours and most preferably from 1 hour to 3 hours.

The amount of the complex catalyst to the unsaturated substrates, in particular the nitrile rubber, depends on the nature and the catalytic activity of the catalyst. The amount of catalyst employed is typically chosen in the range of from 1 to 1000 ppm of noble metal, preferably from 2 to 500 ppm, in particular from 5 to 250 ppm based on the unsaturated substrates, in particular the nitrile rubber used.

The catalyst loading is most preferably 0.040 phr or less.

The catalyst/mole C═C ratio is preferably less than 0.0028%.

Firstly, a solution of the unsaturated substrates, in particular the nitrile rubber in a suitable solvent is prepared. The concentration of the unsaturated substrates, in particular the nitrile rubber in the hydrogenation reaction is not critical, but it should naturally be ensured that the reaction is not adversely affected by an excessively high viscosity of the reaction mixture and any associated mixing problem. The concentration of the unsaturated substrates, in particular the nitrile rubber in the reaction mixture is preferably in the range from 1 to 25% by weight, particularly preferably in the range from 5 to 20% by weight, based on the total reaction mixture.

The hydrogenation reaction is typically carried out in a suitable solvent which does not deactivate the catalyst used and also does not adversely affect the reaction in any other way. Preferred solvents include but are not restricted to dichloromethane, benzene, toluene, monochlorobenzene, methyl ethyl ketone, acetone, methyl isobutyl ketone, tetrahydrofuran, tetrahydropyran, dioxane and cyclohexane. The particularly preferred solvents are monochlorobenzene, methyl ethyl ketone and acetone. The most particularly preferred solvent is monochlorobenzene.

Such solution of the nitrile rubber is then brought into contact with the catalyst according to general formula (I) in the presence of hydrogen at the pressure mentioned above. The reaction mixture is typically stirred or any kind of shear can be introduced to allow sufficient contact of the solution with the hydrogen phase.

One major advantage of the present invention resides in the fact that the complex catalyst used is very active, so that the catalyst residue in the final HNBR products can be low enough to make the catalyst metal removal or recycle step alleviated or even unnecessary. However, to the extent desired, the catalysts used during the process of the present invention may be removed. Such removal can be performed e.g. by using ion-exchange resins as described in EP-A-2 072 532 A1 and EP-A-2 072 533 A1. The reaction mixture obtained after the completion of the hydrogenation reaction can be taken and treated with an ion-exchange resin at e.g. 100° C. for 6 to 48 hours under nitrogen which leads to a bonding of the catalyst to the resin while the reaction mixture can be worked up with the usual finishing methods.

The rubber can then be obtained from the solution by known workup procedures such as steam coagulation, solvent evaporation or precipitation and dried to a degree that allows usage in typical rubber processing methods.

For the purposes of the present invention, hydrogenation is a reaction of the double bonds present in the unsaturated substrates, in particular the nitrile rubber to an extent of at least 50%, preferably 70-100%, more preferably 80-100%, even more preferably 90-100% and most preferably 94-100%.

After the completion of the hydrogenation according to the present invention a hydrogenated nitrile rubber having a Mooney viscosity (ML1+4 at 100° C.), measured in accordance with ASTM standard D 1646, n the range from 1 to 130, preferably from 10 to 100, is obtained. This corresponds to a weight average molecular weight Mw in the range 2,000-400,000 g/mol, preferably in the range 300,000-350,000. The hydrogenated nitrile rubbers obtained also have a polydispersity PDI=Mw/Mn, where Mw is the weight average molecular weight and Mn is the number average molecular weight, in the range 1-5 and preferably in the range 2-4.

The invention is further illustrated but is not intended to be limited by the following examples in which all parts and percentages are by weight unless otherwise specified.

The novel ruthenium- or osmium-based complexes can be used for the selective hydrogenation of nitrile rubber (NBR).

The hydrogenation can be performed as solution hydrogenation or as latex hydrogenation. Aqueous suspensions of diene-based polymers, e.g. nitrile rubber, are called "latex". Such latices contain carbon-carbon double bonds. These latices include both suspensions prepared by free-radical polymerization of aqueous monomer emulsions (primary suspensions) and those whose polymers have been prepared by whatever method or route and are then converted to an aqueous suspension form (secondary suspensions). The term "aqueous suspension" also embraces, in principle, suspensions of microcapsules.

The latex may be prepared by any method known to those skilled in the art, such as emulsion polymerization, solution polymerization or bulk polymerization. Preferably, the latex is prepared in an aqueous emulsion polymerization process as this process directly yields the latex form of the polymer.

The polymer solid content in the aqueous emulsion lies in the range of from 1 to 75% by weight, preferably from 5 to 30% by weight based on the total weight of the aqueous emulsion.

EXAMPLES

Abbreviations phr parts per hundred rubber (weight)
rpm revolution per minute
HD hydrogenation degree [%]
Mn number-average molecular weight
Mw weight-average molecular weight
PDI polydispersity index, defined as Mn/Mw
PPh$_3$ triphenylphosphine
MCB monochorobenzene
r.t. room temperature (22+/−2° C.)
RDB residue double bonds, in %, RDB=100−hydrogenation degree [%] with NBR having an RDB of 100%
NHC N-heterocyclic-carbene
Cy cyclohexyl
Et$_3$N triethylamine
IMes N,N'-bis(mesityl)imidazol-2-ylidene
SIMes N,N'-bis(mesityl)imidazolidin-2-ylidene (also can be called H$_2$-Imes)
IPr N,N'-bis(2,6-diisopropylphenyl)imidazol-2-ylidene
SIPr N,N'-bis(2,6-diisopropylphenyl)imidazolidin-2-ylidene
ItBu N,N'-bis(tert-butyl)imidazol-2-ylidene A. Preparation of Catalysts General Procedures:

The following scheme shows different routes to prepare the inventive ruthenium- or osmium-based complex catalysts:

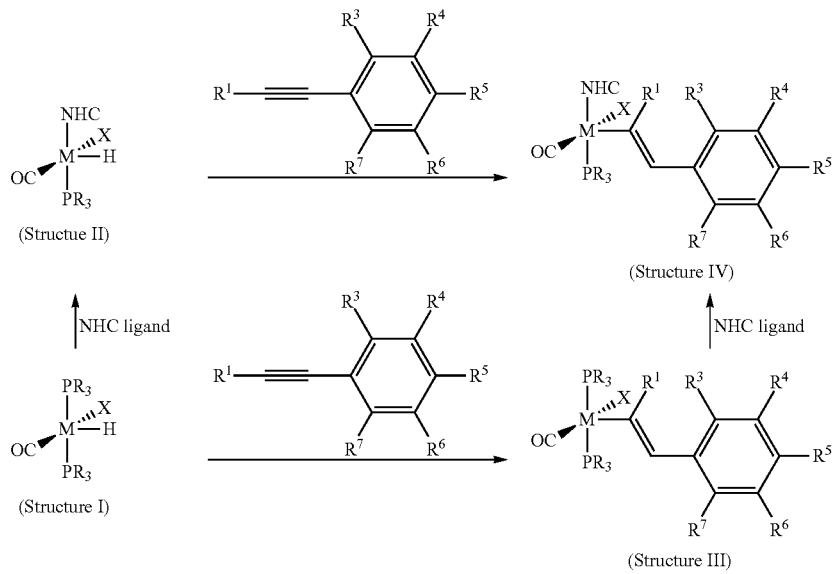

(Structure II)

(Structure IV)

(Structure I)

(Structure III)

Catalysts of structure I are known from U.S. Pat. No. 5,057,581.

Catalysts of structure II are known from WO-A-2013/159365.

Catalysts of structure III are known from Müke, P., et al. Inorganica Chmica Acta 374 (2011) 36-50.

Structure IV represents inventive ruthenium- or osmium-based complex catalysts falling under the general formula I.

Reactions were done using standard Schlenk and glove-box techniques, unless noted differently. Solvents were purchased from Sigma-Aldrich (ACS purity grade, 99.5%) and used in dried form and stored under $N_2$ or Ar.

N,N'-bis(mesityl)imidazol-2-ylidene (IMes) and N,N'-bis(mesityl)imidazolidin-2-ylidene (SIMes) were purchased from Sigma-Aldrich.

The following complex catalysts A, B.a, I.a, I.b, I.c, I.e, g, I.g, I.k and I.m were prepared as outlined below:

Catalyst A: RUHCl(CO)(PCy$_3$)$_2$ (Comparative Example)

The complex was prepared following a procedure by James at al, (Adv. In Chem., 1982, 196, 145-161 as follows: RuCl$_3$×H$_2$O (0.635 g, 2.5 mmol) was dissolved in methoxy-ethanol (15 mL). After 5 minutes PCy$_3$ (2.056 g, 7.5 mmol) was added. The mixture was heated under reflux for 20 minutes. Then Et$_3$N (2 mL) was added. The mixture was heated under reflux for another 6 hours and then cooled. The crystalline orange product was filtered and then washed with toluene (10 mL×2) and dried in vacuum. The yield obtained was 1.45 g (80%) as yellow crystals. The FT-IR on a saturated solution in MCB gave a single peak (CO) at 1901 cm$^{-1}$ and was thus considered to be free from the possible by-product RuHCl(CO)$_2$(PCy$_3$)$_2$.

Catalyst B.a: RuHCl(CO)(IMes)(PCy$_3$) (Comparative Example)

The complex was prepared by reacting RuHCl(CO)(PCy$_3$)$_2$ (Catalyst A) with IMes following the procedure in Nolan at al (Organometallics 2001, 20, 794) as follows: A 100 mL flask was charged with RuHCl(CO)(PCy$_3$)$_2$ (510 mg, 0.7 mmol) and IMes (302 mg, 1.05 mmol) and degassed. Then 20 mL toluene were added via a syringe. Then the solution was heated at 80° C. for 2 hours and stirred for 18 hours at room temperature. The solution was removed under vacuum. The orange-yellow residue was taken up in 20 mL ethanol (degassed and dried). Then the suspension was filtered. The precipitate was washed with ethanol (20 mL×3) and dried under vacuum. The yield obtained was 125.7 mg as orange crystals with a single peak (CO) at 1897 cm$^{-1}$ (lit. 1896 cm$^{-1}$ in CH$_2$Cl$_2$).

Catalyst I.a: Ru(CH=CHPh)Cl(CO)(IMes)(PCy$_3$) (Inventive Example)

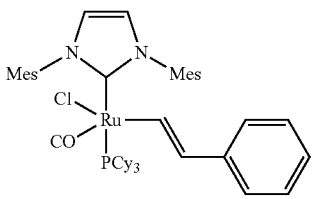

This complex was prepared by reacting RuHCl(CO)(IMes)(PCy$_3$) (Catalyst B.a) with phenyl acetylene as follows: 2 g of RuHCl(CO)(IMes)(PCy$_3$) were dissolved in 50 mL of dichloromethane at room temperature under Ar atmosphere, and then 0.298 g of phenyl acetylene were added into the solution. After the mixing at room temperature for 4 hours, 30 mL of iso-propanol were added into the mixture to precipitate the obtained Ru(CH=CHPh)Cl(CO)(IMes)(PCy$_3$) under Ar. After filtration, the precipitated catalyst was washed with 15 mL of iso-propanol and dried under vacuum to finally obtain 1.83 g of the catalyst (80.5% yield).

The color of catalyst 1a, Ru(CH=CHPh)Cl(CO)(IMes)(PCy$_3$), did not change after one week exposed to air, in water or in MCB solution under air, which indicate its very good stability.

Catalyst I.b: Ru(CH=CHPh)Cl(CO)(SIMes)(PCy$_3$)
(Inventive Example)

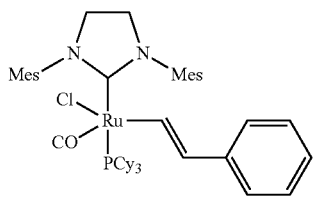

This complex was prepared by reacting RuHCl(CO)(SIMes)(PCy$_3$)(Catalyst B.b) with phenyl acetylene as follows: 0.652 g of RuHCl(CO)(SIMes)(PCy$_3$) were dissolved in 16 mL of dichloromethane at room temperature under Ar atmosphere, and then 0.097 g of phenyl acetylene were added into the solution. After the mixing at room temperature for 4 hours, 10 mL of iso-propanol were added into the mixture to precipitate the obtained Ru(CH=CHPh)Cl(CO)(SIMes)(PCy$_3$) under Ar. After filtration, the precipitated catalyst was washed with 5 mL of iso-propanol and dried under vacuum to finally obtain 0.41 g of the catalyst (55.4% yield).

Catalyst I.e: Ru(CH=CHPh-OCH$_3$)Cl(CO)(IMes)(PCy$_3$)(Inventive Example)

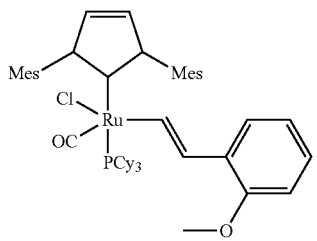

This complex was prepared by reacting RuHCl(CO)(IMes)(PCy$_3$) with 2-Ethynylanisole as follows: 2.5 g of RuHCl(CO)(IMes)(PCy$_3$) were dissolved in 30 mL of dichloromethane at room temperature under Ar atmosphere, and then 0.482 g of 2-Ethynylanisole were added into the solution. After the mixing at room temperature for 4 hours, 40 mL of iso-propanol were added into the mixture to precipitate the obtained catalyst under Ar. After filtration, the precipitated catalyst was washed with 20 mL of iso-propanol first and then with 10 mL of n-hexane and dried under vacuum to finally obtain 2.514 g of the catalyst (85.4% yield).

Catalyst I.c: Ru(CH=CHPh-OiPr)Cl(CO)(IMes)(PCy$_3$) (Inventive Example)

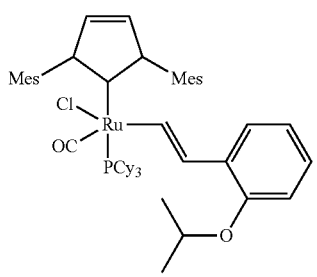

This complex was prepared by reacting RuHCl(CO)(IMes)(PCy$_3$) (Catalyst B.a) with 1-Ethynyl-2-isopropoxybenzene (prepared according to the procedures described by Alois Fürstner et al. Organometallics 2005, 24, 4065-4071) as follows: 4 g of RuHCl(CO)(IMes)(PCy$_3$) were dissolved in 30 mL of dichloromethane at room temperature under Ar atmosphere, and then 0.9 g of 1-Ethynyl-2-isopropoxybenzene were added into the solution. After the mixing at room temperature for 4 hours, 64 mL of iso-propanol were added into the mixture to precipitate the obtained catalyst under Ar. After filtration, the precipitated catalyst was washed with 30 mL of iso-propanol first and then with 15 mL of n-hexane and dried under vacuum to finally obtain 2.73 g of the catalyst (56.2% yield).

Catalyst I.g: Ru(CH=CHPh-OCH$_3$)Cl(CO)(IMes)(PCy$_3$)(Inventive Example)

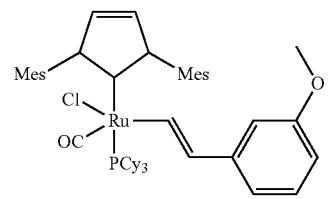

This complex was prepared by reacting RuHCl(CO)(IMes)(PCy$_3$) (Catalyst B.a) with 3-Ethynylanisole as follows: 1 g of RuHCl(CO)(IMes)(PCy$_3$) was dissolved in 12 mL of dichloromethane at room temperature under Ar atmosphere, and then 0.195 g of 3-Ethynylanisole were added into the solution. After the mixing at room temperature for 4 hours, 16 mL of iso-propanol were added into the mixture to precipitate the obtained catalyst under Ar. After filtration, the precipitated catalyst was washed with 8 mL of iso-propanol first and then with 4 mL of n-hexane and dried under vacuum to finally obtain 0.415 g of the catalyst (35.2% yield).

Catalyst I.m: Ru[CH=CHPh-(COOCH$_3$)$_2$]Cl(CO)(IMes)(PCy$_3$)(Inventive Example)

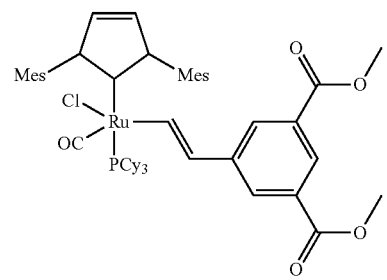

This complex was prepared by reacting RuHCl(CO)(IMes)(PCy$_3$) (Catalyst B.a) with Dimethyl-5-ethynylisophthalate as follows: 0.75 g of RuHCl(CO)(IMes)(PCy$_3$) were dissolved in 9 mL of dichloromethane at room temperature under Ar atmosphere, and then 0.241 g of Dimethyl-5-ethynylisophthalate were added into the solution. After the mixing at room temperature for 4 hours, 12 mL of iso-propanol were added into the mixture to precipitate the obtained catalyst under Ar. After filtration, the precipitated catalyst was washed with 6 mL of iso-propanol first and then with 3 mL of n-hexane and dried under vacuum to finally obtain 0.832 g of the catalyst (85.8% yield).

Catalyst I.i: Ru(CH=CHPh-OCH$_3$)Cl(CO)(IMes)(PCy$_3$)(Inventive Example)

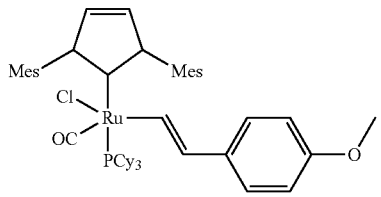

This complex was prepared by reacting RuHCl(CO)(IMes)(PCy$_3$) (Catalyst B.a) with 4-Ethynylanisole as follows: 0.75 g of RuHCl(CO)(IMes)(PCy$_3$) were dissolved in 9 mL of dichloromethane at room temperature under Ar atmosphere, and then 0.145 g of 4-Ethynylanisole were added into the solution. After the mixing at room temperature for 4 hours, 12 mL of iso-propanol were added into the mixture to precipitate the obtained catalyst under Ar. After filtration, the precipitated catalyst was washed with 6 mL of iso-propanol first and then with 3 mL of n-hexane and dried under vacuum to finally obtain 0.71 g of the catalyst (80.4% yield)

Catalyst I.k: Ru[CH=CHPh-(OCH$_3$)$_2$]Cl(CO)(IMes)(PCy$_3$)(Inventive Example)

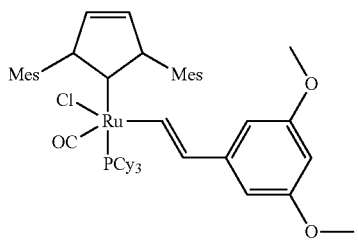

This complex was prepared by reacting RuHCl(CO)(IMes)(PCy$_3$) (Catalyst B.a) with 1-Ethynyl-3,5-dimethoxybenzene as follows: 0.75 g of RuHCl(CO)(IMes)(PCy$_3$) were dissolved in 9 mL of dichloromethane at room temperature under Ar atmosphere, and then 0.176 g of 1-Ethynyl-3,5-dimethoxybenzene were added into the solution. After the mixing at room temperature for 4 hours, 12 mL of iso-propanol was added into the mixture to precipitate the obtained catalyst under Ar. After filtration, the precipitated catalyst was washed with 6 mL of iso-propanol first and then with 3 mL of n-hexane and dried under vacuum to finally obtain 0.71 g of the catalyst (77.7% yield).

B Nitrile Butadiene Rubbers

The nitrile butadiene rubbers which were used in the examples are all commercially available from Lanxeass Deutschland GmbH and have the properties as outlined in Table 1 below.

TABLE 1

Nitrile Butadiene Rubbers (NBR) used

| NBR | Acrylonitrile content [% by weight] | Mooney viscosity ML(1 + 4)@ 100° C. [MU] | Mn [g/mol] | Mw [g/mol] | PDI |
|---|---|---|---|---|---|
| NBR-1 | 34 | 33 | 70.674 | 251.292 | 3.56 |
| NBR-2 | 34 | 35 | 71.433 | 282.637 | 3.96 |

MU = Mooney units

C Hydrogenation of Nitrile Rubber

Catalysts were used in amounts in the range of from 0.015 to 0.04 phr as shown in the subsequent tables under Section E.

The conditions for hydrogenation were:
8.3 MPa (1200 psi) hydrogen pressure
600 rpm of agitation
Temperature: 138° C. as shown in the subsequent tables.
Time: variable depending on the progress of hydrogenation as shown in the subsequent tables.

Hydrogenation Procedure:
(1) The nitrile rubber was dissolved in a certain amount of MCB to form NBR solution with different solid contents. The solution was filled in an autoclave (2 L volume) and bubbled with nitrogen gas for 20 minutes to remove dissolved oxygen.
(2) Under nitrogen protection, catalyst was dissolved in a sufficient amount of degassed MCB. Under nitrogen protection the solution was transferred into a stainless pressurable vessel connected with a valve to the autoclave via syringe.
(3) After the autoclave was heated to desired temperature, the catalyst solution was transferred into the autoclave by applying hydrogen pressure. Then the hydrogen pressure was raised to desired value.
(4) Samples were taken out at intervals for FT-IR test to monitor the RDB.
(5) After the finish of NBR hydrogenation, the solution was cooled down and the pressure was released. Finally the HNBR crumbs were isolated by steam-coagulation and dried under vacuum.

D Analysis and Tests

Measurement of Molecular Weights Mn and Mw by GPC:

The molecular weights Mn and Mw were determined by a Waters GPC system equipped with a Waters 1515 high performance liquid chromatography pump, a Waters 717 plus autosampler, a PL gel 10 μm mixed B column and a Waters 2414 RI detector. The GPC test was carried out at 40° C. at 1 mL/min of flow rate with THF as the eluent, and the GPC column was calibrated with narrow PS standard samples.

Measurement of the Hydrogenation Degree and the Residual Double Bonds ("RDB") by FT-IR:

The spectrum of nitrile rubber before, during and after the hydrogenation reaction was recorded on a Perkin Elmer spectrum 100 FT-IR spectrometer. The solution of the (hydrogenated) nitrile butadiene rubber in MCB was cast onto a KBr disk and dried to form a film for the test. The hydrogenation degree was determined by the FT-IR analysis according to the ASTM D 5670-95 method. The residual double bonds, RDB, can be calculated to be 100–hydrogenation degree [%].

E Hydrogenation Experiments

CEx. 1

Hydrogenation of NBR-2 Catalyzed by Catalyst B.a (RuHCl(CO)(IMes)(PCy$_3$))

100 grams of NBR-2 were dissolved in MCB to form a 13 wt % of NBR solution. Catalyst B.a was used at the loading of 20 mg (0.02 phr).

Ex. 1

Hydrogenation of NBR-2 Catalyzed by Catalyst I.c (Ru(CH=CHPh-OiPr)Cl(CO)(IMes)(PCy$_3$))

100 grams of NBR-2 were dissolved in MCB to form a 13 wt % of NBR solution. Catalyst I.c was used at the loading of 20 mg (0.02 phr).

Ex. 2

Hydrogenation of NBR-2 Catalyzed by Catalyst I.m (Ru[CH=CHPh-(COOCH$_3$)$_2$]Cl(CO)(IMes)(PCy$_3$))

100 grams of NBR-2 were dissolved in MCB to form a 13 wt % of NBR solution. Catalyst I.m was used at the loading of 20 mg (0.02 phr).

Ex. 3

Hydrogenation of NBR-2 Catalyzed by Catalyst I.i: (Ru(CH=CHPh-OCH$_3$)Cl(CO)(IMes)(PCy$_3$))

100 grams of NBR-2 were dissolved in MCB to form a 13 wt % of NBR solution. Catalyst I.i was used at the loading of 20 mg (0.02 phr).

Ex. 4

Hydrogenation of NBR-2 Catalyzed by Catalyst I.b: Ru(CH=CHPh)Cl(CO)(SIMes)(PCy$_3$)

100 grams of NBR-2 were dissolved in MCB to form a 13 wt % of NBR solution. Catalyst I.b was used at the loading of 20 mg (0.02 phr).

Hydrogenation results of CEx. 1, Ex. 1, Ex. 2, Ex. 3 and Ex. 4 are compared in Table 2 below.

TABLE 2

Different hydrogenation results using 0.02 phr of catalyst B.a, I.c, I.m, I.i and I.b.

| | Hydrogenation degree, RDB [%] | | | | |
|---|---|---|---|---|---|
| reaction time [h] | CEx. 1 Catalyst B.a (0.02 phr) | Ex. 1 Catalyst I.c (0.02 phr) | Ex. 2 Catalyst I.m (0.02 phr) | Ex. 3 Catalyst I.i (0.02 phr) | Ex. 4 Catalyst I.b (0.02 phr) |
| 0 | 100 | 100 | 100 | 100 | 100 |
| 1 | 59 | 26 | 25 | 22 | 60 |
| 2 | 49 | 20 | 17 | 15 | 45 |
| 3 | 41 | 18 | 14 | 12 | 35 |
| 4 | 36 | 18 | 12 | 10 | 29 |
| 5 | 31 | 17 | 11 | 9 | 24 |

CEx. 2

Hydrogenation of NBR-2 Catalyzed by Catalyst B.a: RuHCl(CO)(IMes)(PCy$_3$)

100 grams of NBR-2 were dissolved in MCB to form a 13 wt % of NBR solution. Catalyst B.a was used at the loading of 30 mg (0.03 phr).

Ex. 5

Hydrogenation of NBR-2 Catalyzed by Catalyst I.g: Ru(CH=CHPh-OCH$_3$)Cl(CO)(IMes)(PCy$_3$)

100 grams of NBR-2 were dissolved in MCB to form a 13 wt % of NBR solution. Catalyst I.g was used at the loading of 30 mg (0.03 phr).

Ex. 6

Hydrogenation of NBR-2 Catalyzed by Catalyst I.h: Ru[CH=CHPh-(OCH)]Cl(CO)(IMes)(PCy$_3$)

100 grams of NBR-2 were dissolved in MCB to form a 13 wt % of NBR solution. Catalyst I.h was used at the loading of 40 mg (0.04 phr).

Hydrogenation results of CEx. 2, Ex. 5 and Ex. 6 are compared in the Table 4 below:

TABLE 4

Different hydrogenation results using 0.03 phr of Catalyst B.a and I.g and 0.04 phr of I.h.

| | Hydrogenation degree, RDB [%] | | |
|---|---|---|---|
| reaction time [h] | CEx. 2 Catalyst B.a (0.03 phr) | Ex. 5 Catalyst I.g (0.03 phr) | Ex. 6 Catalyst I.h (0.04 phr) |
| 0 | 100 | 100 | 100 |
| 1 | 9 | 4 | 1 |
| 2 | 3 | 1 | <1 |
| 3 | 1 | <1 | — |
| 4 | <1 | — | — |

CEx. 3

Hydrogenation of NBR-1 Catalyzed by Catalyst B.a: RuHCl(CO)(IMes)(PCy$_3$)

100 grams of NBR-1 were dissolved in MCB to form a 13 wt % of NBR solution. Catalyst B.a was used at the loading of 20 mg (0.02 phr).

Ex. 7

Hydrogenation of NBR-1 Catalyzed by Catalyst I.e: Ru(CH=CHPh-OCH$_3$)Cl(CO)(IMes)(PCy$_3$)

100 grams of NBR-1 was dissolved MCB to form a 13 wt % of NBR solution. Catalyst I.e was used at the loading of 20 mg (0.02 phr).

Ex. 8

Hydrogenation of NBR-1 Catalyzed by Catalyst I.a: Ru(CH=CHPh)Cl(CO)(IMes)(PCy₃)

100 grams of NBR-1 were dissolved in MCB to form a 13 wt % of NBR solution. Catalyst I.a was used at the loading of 20 mg (0.02 phr).

Ex. 9

Hydrogenation of NBR-1 Catalyzed by Aged Catalyst I.a: Ru(CH=CHPh)Cl(CO)(IMes)(PCy₃)

100 grams of NBR-1 were dissolved in MCB to form a 13 wt % of NBR solution. Catalyst I.a was exposed to air at room temperature for one week and then used at the loading of 20 mg (0.02 phr).

Ex. 10

Hydrogenation of NBR-1 Catalyzed by Catalyst I.a: Ru(CH=CHPh)Cl(CO)(IMes)(PCy₃)

100 grams of NBR-1 were dissolved in MCB to form a 13 wt % of NBR solution. Catalyst I.a was used at the loading of 15 mg (0.015 phr).

Hydrogenation results of CEx. 3, Ex. 7, Ex. 8, Ex. 9 and Ex. 10 are compared in the Table 5 below:

TABLE 5

Different hydrogenation results using 0.02 phr of catalyst B.a, I.e and I.a and 0.015 phr of I.a

| | | Hydrogenation degree, RDB [%] | | | |
|---|---|---|---|---|---|
| reaction time [h] | CEx. 3 Catalyst B.a (0.02 phr) | Ex. 7 Catalyst I.e (0.02 phr) | Ex. 8 Catalyst I.a (0.02 phr) | Ex. 9 Catalyst I.a* (0.02 phr) | Ex. 10 Catalyst I.a (0.015 phr) |
| 0 | 100 | 100 | 100 | 100 | 100 |
| 1 | 36 | 9 | 5 | 7 | 12 |
| 2 | 18 | 4 | 2 | 3 | 5 |
| 3 | 10 | 3 | 1 | 2 | 4 |
| 4 | 7 | 2 | <1 | 1 | 3 |
| 5 | 5 | 2 | — | <1 | 2 |

*Catalyst I.a was exposed to air at room temperature for one week

Overview of all Hydrogenation Results [%] of all Experiments

| | | Load | | Reaction time [h] | | | | | |
|---|---|---|---|---|---|---|---|---|---|
| # | Cat. | [phr] | NBR | 0 | 1 | 2 | 3 | 4 | 5 |
| CEx. 1 | B.a | 0.02 | NBR-2 | 100 | 59 | 49 | 41 | 36 | 31 |
| CEx. 2 | B.a | 0.03 | NBR-2 | 100 | 9 | 3 | 1 | <1 | |
| CEx. 3 | B.a | 0.02 | NBR-1 | 100 | 36 | 18 | 10 | 7 | 5 |
| Ex. 1 | I.c | 0.02 | NBR-2 | 100 | 26 | 20 | 18 | 18 | 17 |
| Ex. 2 | I.m | 0.02 | NBR-2 | 100 | 25 | 17 | 14 | 12 | 11 |
| Ex. 3 | I.l | 0.02 | NBR-2 | 100 | 22 | 15 | 12 | 10 | 9 |
| Ex. 4 | I.b | 0.02 | NBR-2 | 100 | 60 | 45 | 35 | 29 | 24 |
| Ex. 5 | I.g | 0.03 | NBR-2 | 100 | 4 | 1 | <1 | — | |
| Ex. 6 | I.h | 0.04 | NBR-2 | 100 | 1 | <1 | — | — | |
| Ex. 7 | I.e | 0.02 | NBR-1 | 100 | 9 | 4 | 3 | 2 | 2 |
| Ex. 8 | I.a | 0.02 | NBR-1 | 100 | 5 | 2 | 1 | <1 | — |
| Ex. 9 | I.a* | 0.02 | NBR-1 | 100 | 7 | 3 | 2 | 1 | <1 |
| Ex. 10 | I.a | 0.015 | NBR-1 | 100 | 12 | 5 | 4 | 3 | 2 |

The above examples clearly show that, at the same wt % of catalyst loading, these novel Ru—NHC-vinyl-ligand catalysts according to the general formula (I) performed better in the hydrogenation of nitrile rubber than the structurally close catalysts Ru—NHC-hydrogen (such as RuHCl(CO)(IMes)(PCy₃)). Since these Ru—NHC-vinyl-ligand catalysts have higher molecular weight than the original Ru—NHC-hydrogen catalysts, this indicates that every mole of the Ru—NHC-vinyl-ligand catalyst is more active than the same mole of the original Ru—NC-hydrogen catalysts.

What is claimed is:

1. A complex having the general formula (I)

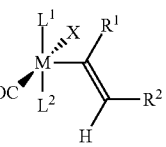

(I)

wherein
M represents ruthenium or osmium,
X represents F, Cl, Br, I, —OH, —CF₃, pyridine, —OC₆H₅, —CF₃COO⁻, —CH₃SO₃⁻, or —BF₄⁻,
L¹ represents a N-heterocyclic carbene (NHC) ligand,
L² represents a phosphine ligand,
R¹ represents hydrogen,
R² represents
straight chain or branched, substituted or unsubstituted C₁-C₁₄-alkyl; or
substituted or unsubstituted C₃-C₁₀-cycloalkyl; or
substituted or unsubstituted C₆-C₁₄-aryl.

2. The complex according to claim 1, wherein:
M, L¹, L², X and R¹ have the same meanings as given in claim 1, and
R² represents

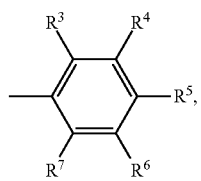

wherein R³, R⁴, R⁵, R⁶ and R⁷ are each individually of each other
H, NO₂, F, Cl, Br, I or CN; or
straight chain or branched, substituted or unsubstituted C₁-C₁₄-alkyl; or
substituted or unsubstituted C₃-C₁₀-cycloalkyl; or
substituted or unsubstituted C₅-C₁₄-aryl; or
Pyren, Perylen, Benz(a)pyren; or
OR¹², OC(=O)R¹², C(=O)OR¹², SO₃R¹², SO₃N(R¹²)₂ or SO₃Na wherein R¹² represents H, straight chain or branched, substituted or unsubstituted C₁-C₁₄-alkyl; or
(N(R¹³)₃)⁺X⁻ wherein X is halide, and R¹³ are identical or different and represent H; straight chain or branched, substituted or unsubstituted C₁-C₁₄-alkyl; substituted or unsubstituted C₆-C₁₄-aryl; or
tris (C₁-C₆-alkoxy)silyl-C₁-C₆-alkyl, tris (C₆-C₁₄-aryloxy)silyl-C₁-C₆-alkyl, or tris (C₃-C₁₀-cycloalkoxy)silyl-C₁-C₆-alkyl.

3. The complex according to claim 2, wherein
wherein $R^3$, $R^4$, $R^5$, $R^6$ and $R^7$ are each individually of each other
H, $NO_2$, F, Cl, Br, I or CN; or
methyl, ethyl, n-propyl, iso-propyl, n-butyl, iso-butyl, or tert.-butyl; or
cyclopentyl, cyclohexyl or cycloheptyl; or
unsubstituted phenyl, or phenyl comprising 1, 2, 3, 4 or 5 identical or different substituents; or
Pyren, Perylen, Benz(a)pyren; or
$OR^{12}$, $OC(=O)R^{12}$, $C(=O)OR^{12}$, $SO_3^{12}$, $SO_3N(R^{12})_2$ or $SO_3Na$ wherein $R^{12}$ represents H, methyl, ethyl, n-propyl, iso-propyl, n-butyl, iso-butyl, or tert.-butyl; or
$N(CH_3)(C_2H_5)_2{}^+Cl^-$, $N(C_2H_5)_2H^+Cl^-$, $NH_3{}^+Cl^-$, $NH(CH_3)_2{}^+Cl^-$, or $N(CH_3)_3{}^+Cl^-$; or trisethoxysilyl-n-propyl.

4. The complex according to claim 1, wherein the N-heterocyclic carbene ligand $L^1$ represents a cyclic carbene ligand with at least one nitrogen as hetero atom being present in the ring.

5. The complex according to claim 1, wherein the NHC-ligand has the structures (IIIa) to (IIIu), where "Ph" stands in each case for phenyl, "Bu" stands in each case for butyl, i.e. either n-butyl, sec.-butyl, iso-butyl or tert.-butyl, "Mes" stands in each case for 2,4,6-trimethylphenyl, "Dipp" stands in each case for 2,6-diisopropylphenyl and "Dimp" stands in each case for 2,6-dimethylphenyl

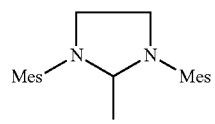 (IIIa)

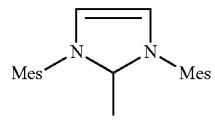 (IIIb)

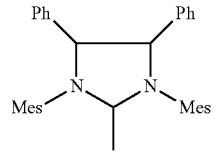 (IIIc)

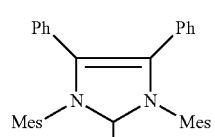 (IIId)

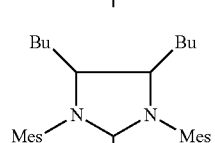 (IIIe)

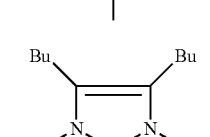 (IIIf)

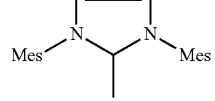

-continued

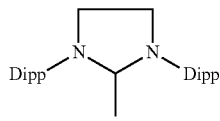 (IIIg)

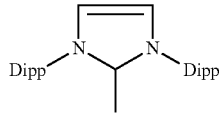 (IIIh)

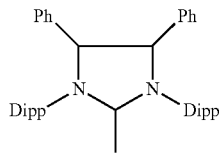 (IIIj)

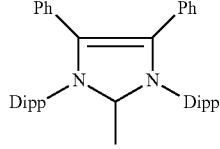 (IIIk)

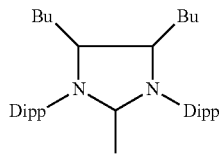 (IIIm)

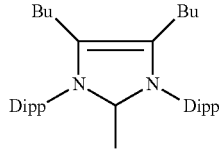 (IIIn)

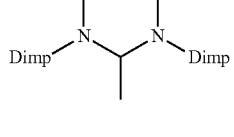 (IIIp)

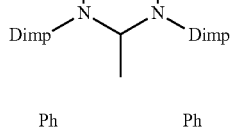 (IIIq)

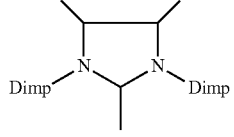 (IIIr)

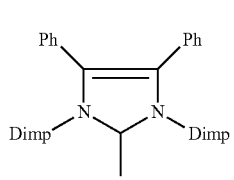 (IIIs)

-continued

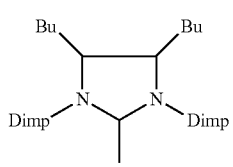
(IIIt)

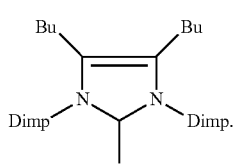
(IIIu)

6. The complex according to claim 1, wherein
M represents ruthenium,
L¹ represents N,N'-bis(mesityl)imidazole-2-ylidne, N,N'-bis(mesityl)imidazoldine-2-ylidene, N,N'-bis(2.6-diisopropylphenyl)imidazoline-2-ylidene or N,N'-bis(2, 6-diisopropylphenyl)imidazolidine2-ylidene,
L² represents $PCy_3$ or $PPh_3$,
X represents Cl,
R¹ represents hydrogen,
R² represents

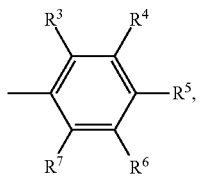

wherein R³, R⁴, R⁵, R⁶ and R⁷ are each individually or each other hydrogen, —C(=O)OCH₃, methoxy, ethoxy or iso-propoxy.

7. The complex according to claim 1, wherein
M represents ruthenium,
L¹ represents N,N'-bis(mesityl)imidazole-2-ylidne or N,N'-bis(mesityl)imidazolidine-2-ylidene,
L² represents $PCy_3$,
X represents Cl,
R¹ represents hydrogen,
R² represents

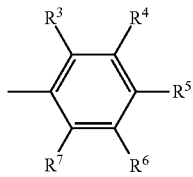

wherein R³, R⁴, R⁵, R⁶ and R⁷ are each individually of each other hydrogen, methoxy, ethoxy or iso-propoxy.

8. The complex according to claim 1, wherein R² represents:
methyl, ethyl, n-propyl, iso-propyl, n-butyl, iso-butyl, or tert.-butyl; or
cyclopentyl, cyclohexyl or cycloheptyl; or
unsubstituted phenyl, or phenyl comprising 1, 2, 3, 4 or 5 identical or different substituents.

9. The complex according to claim 1, wherein the N-heterocyclic carbene ligand L¹ represents a structure corresponding to the general formulae (IIa) to (IIg):

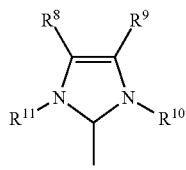
(IIa)

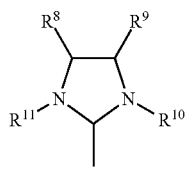
(IIb)

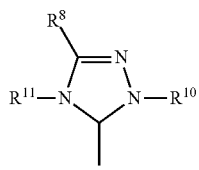
(IIc)

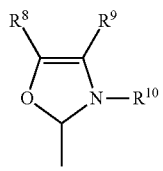
(IId)

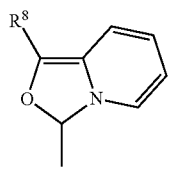
(IIe)

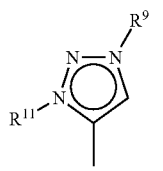
(IIf)

(IIg)

wherein
R⁸, R⁹, R¹⁰ and R¹¹ are identical or different and represent hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_7$-$C_{25}$-alkaryl, $C_2$-$C_{20}$-heteroaryl, $C_2$-$C_{20}$-heterocyclyl, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-aralkoxycarbonyl, $C_1$-$C_{20}$-alkylthio, $C_6$-$C_{20}$-arylthio, —Si(R)₃, —O—Si(R)₃, —O—C(=O)R, C(=O)R, —C(=O)N(R)₂, —NR—C(=O)—N(R)₂, —SO₂N(R)₂, —S(=O)R, —S(=O)₂R, —O—S(=O)₂R, halogen, nitro or cyano; wherein in all above occurrences relating to the meanings of R⁸, R⁹, R¹⁰ and R¹¹ the group R is identical or different and represents hydrogen, $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl or $C_2$-$C_{20}$-heteroaryl, and wherein $R^8$, $R^9$, $R^{10}$ and $R^{11}$, independently of one another, are unsubstituted or substituted by one or more substituents selected from straight-chain or branched $C_1$-$C_{10}$-alkyl, $C_3$-$C_8$-cycloalkyl, $C_1$-$C_{10}$-alkoxy, $C_6$-$C_{24}$-aryl, $C_2$-$C_{20}$ heteroaryl, $C_2$-$C_{20}$ heterocyclic, a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein the abovementioned substituents are independently of one another either unsubstituted or substituted by one or more
substituents selected from the group consisting of chlorine or bromine, $C_1$-$C_5$-alkyl, $C_1$-$C_5$-alkoxy and phenyl.

10. The complex according to claim 9, wherein
$R^8$ and $R^9$ are identical or different and represent hydrogen, $C_6$-$C_{24}$-aryl, straight-chain or branched $C_1$-$C_{10}$-alkyl, or form a cycloalkyl or aryl structure together with the carbon atoms to which they are bound, and
$R^{10}$ and $R^{11}$ are identical or different and represent straight-chain or branched $C_1$-$C_{10}$-alkyl, $C_3$-$C_{10}$-cycloalkyl, substituted or unsubstituted $C_6$-$C_{24}$-aryl, $C_1$-$C_{10}$-alkylsulfonate, or $C_8$-$C_{10}$-arylsulfonate.

11. The complex according to claim 9, wherein
$R^8$ and $R^9$ are identical or different and represent hydrogen, phenyl, methyl, ethyl, n-propyl, iso-propyl, n-butyl, sec-butyl, and iso-butyl, or form a cycloalkyl or aryl structure together with the carbon atoms to which they are bound, and
$R^{10}$ and $R^{11}$ are identical or different and represent iso-propyl or n-pentyl, adamantyl, phenyl, 2,6-diisopropylphenyl, 2,6-dimethylphenyl, 2,4,6-trimethylphenyl, $C_1$-$C_{10}$-alkyisulfonate, or $C_6$-$C_{10}$-arylsulfonate.

12. A process of preparing the complex of the general formula (I) according to claim 1, the process comprising the step of: reacting a compound of general formula (1)

$$MHX(CO)L^1L^2 \quad (1)$$

wherein
M represents ruthenium or osmium,
X represents F, Cl, Br, I, —OH, —$CF_3$, pyridine, —$OC_6H_5$, —$CF_3COO^-$, —$CH_3SO_3^-$, or —$BF_4^-$,
$L^1$ represents a N-heterocyclic carbene ligand,
$L^2$ represents a phosphine ligand,
with a compound of general formula (2)

$$R^1—C{\equiv}C—R^2 \quad (2)$$

wherein
$R^1$ represents hydrogen,
$R^2$ represents
H, $NO_2^-$, F, Cl, or Br; or
straight chain or branched, substituted or unsubstituted $C_1$-$C_{14}$-alkyl; or
substituted or unsubstituted $C_3$-$C_{10}$-cycloalkyl; or
substituted or unsubstituted $C_8$-$C_{14}$-aryl.

13. The process according to claim 12, comprising the step of:
reacting a compound of general formula (1) wherein
M represents ruthenium or osmium,
X represents F, Cl, Br, I, —OH, —$CF_3$, pyridine, —$OC_6H_5$, —$CF_3COO^-$, —$CH_3SO_3^-$, or —$BF_4^-$,
$L^1$ represents a N-heterocyclic carbene ligand, and
$L^2$ represents a phosphine ligand, with a compound of general formula (2) wherein
$R^1$ represents hydrogen and
$R^2$ represents

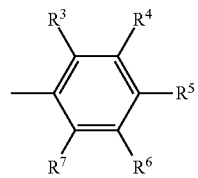

wherein $R^3$, $R^4$, $R^5$, $R^6$ and $R^7$ are each individually of each other H, —$NO_2$, F, Cl, Br, I or —CN; or
straight chain or branched, substituted or unsubstituted $C_1$-$C_{14}$-alkyl; or
substituted or unsubstituted $C_3$-$C_{10}$-cycloalkyl; or
substituted or unsubstituted $C_6$-$C_{14}$-aryl; or
Pyren, Perylen, Benz(a)pyren; or
—$OR^{12}$, —$OC({=}O)R^{12}$, —$C({=}O)OR^{12}$, —$SO_3R^{12}$, —$SO_3N(R^{12})_2$ or —$SO_3Na$ wherein $R^{12}$ represents H, straight chain or branched, substituted or unsubstituted $C_1$-$C_{14}$-alkyl; or
—$(N(R^{13})_3)^+X^-$ wherein X is halide, and $R^{13}$ are identical or different and represent H; straight chain or branched, substituted or unsubstituted $C_1$-$C_{14}$-alkyl, substituted or unsubstituted $C_6$-$C_{14}$-aryl; or
tris ($C_1$-$C_8$-alkoxy)silyl-$C_1$-$C_6$-alkyl, tris ($C_6$-$C_{14}$-aryloxy)silyl-$C_1$-$C_6$-alkyl, or tris ($C_3$-$C_{10}$-cycloalkoxy)silyl-$C_1$-$C_6$-alkyl, or trisethoxysilyl-n-propyl.

14. The process according to claim 12, wherein:
the compound of general formula (1) is selected from the group consisting of;
RuHCl(CO)(N,N'-bis(mesity)imidazole-2-ylidne) (PCy$_3$), RuHCl(CO)(N,N'-bis(mesityl)imidazolidine-2-ylidene)(PCy$_3$), RuHCl(CO)(IPr)(PCy$_3$), RuHCl(CO)(N,N'-bis(2,6-diisopropylphenyl)imidazolidine-2-ylidene)(PCy$_3$), RuHCl(CO)(N,N'-bis(mesityl)imidazole-2-ylidne)(PPh$_3$), RuHCl(CO)(N,N'-bis(mesityl)imidazolidine-2-ylidene)(PPh$_3$), RuHCl(CO)(IPr)(PPh$_3$) and RuHCl(CO)(N,N'-bis(2,6-diisopropylphenyl)imidazolidine-2-ylidene)(PPh$_3$, and,
the compound of general formula (2) is selected from the group consisting of;
phenyl acetylene, 1-Ethynyl-2-isopropoxybenzene, 1-Ethynyl-3-isopropoxybenzene, 2-Ethynylanisole, 3-Ethynylanisole, 4-Ethynylanisole, 1-Ethynyl-3,5-dimethoxybenzene and Dimethyl-5-ethynylisophthalate.

15. A process of preparing partially or fully saturated compounds, the process comprising the step of: contacting unsaturated compounds comprising at least one C=C double bond with hydrogen in the presence of the complex according to claim 1.

16. A process of preparing partially or fully hydrogenated nitrite rubbers comprising the step of: bringing a solution of unsaturated nitrile rubber, or bringing a latex of unsaturated nitrile rubber in contact with hydrogen in the presence of the complex according to claim 1.

17. The process according to claim 16, whereas nitrile rubbers represent copolymers or terpolymers comprising repeating units based on (i) at least one conjugated diene, (ii) at least one α,β-unsaturated nitrile monomer.

18. The process according to claim 16, wherein the process comprises the step of: bringing a latex of unsaturated nitrile rubber in contact with hydrogen, and further comprises the step of preparing the latex in an aqueous emulsion polymerization process.

\* \* \* \* \*